(12) United States Patent
Park et al.

(10) Patent No.: US 12,226,768 B2
(45) Date of Patent: Feb. 18, 2025

(54) POLYMERASE CHAIN REACTION SYSTEM

(71) Applicant: Bioneer Corporation, Daejeon (KR)

(72) Inventors: Han Oh Park, Sejong-si (KR); Jong Kab Kim, Gyeongsangbuk-do (KR); Yang Won Lee, Daejeon (KR); Sang Ryoung Park, Daejeon (KR); Hye Jin Jang, Daejeon (KR)

(73) Assignee: BIONEER CORPORATION, Daejeon (KR)

( * ) Notice: Subject to any disclaimer, the term of this patent is extended or adjusted under 35 U.S.C. 154(b) by 712 days.

(21) Appl. No.: 17/602,665

(22) PCT Filed: Apr. 9, 2020

(86) PCT No.: PCT/KR2020/004840
§ 371 (c)(1),
(2) Date: Oct. 8, 2021

(87) PCT Pub. No.: WO2020/209638
PCT Pub. Date: Oct. 15, 2020

(65) Prior Publication Data
US 2022/0176373 A1    Jun. 9, 2022

(30) Foreign Application Priority Data
Apr. 11, 2019    (KR) .................. 10-2019-0042463

(51) Int. Cl.
*C12Q 1/6806* (2018.01)
*B01L 3/00* (2006.01)
*B01L 7/00* (2006.01)

(52) U.S. Cl.
CPC ... *B01L 3/502715* (2013.01); *B01L 3/502738* (2013.01); *B01L 7/52* (2013.01);
(Continued)

(58) Field of Classification Search
CPC ......... B01L 3/502715; B01L 3/502738; B01L 2200/04; B01L 2200/10; B01L 2200/147;
(Continued)

(56) References Cited

U.S. PATENT DOCUMENTS 6,767,512 B1    7/2004    Lurz et al.
2014/0220579 A1    8/2014    de Vos
(Continued)

FOREIGN PATENT DOCUMENTS

CN    101711257 A    5/2010
CN    201828516 U    5/2011
(Continued)

OTHER PUBLICATIONS

Search Report issued in European Patent Application No. 20788280.4, May 13, 2022.

*Primary Examiner* — Brian J. Sines
(74) *Attorney, Agent, or Firm* — Morse, Barnes-Brown & Pendleton, P.C.; Martin Z. Zhang, Esq.

(57) ABSTRACT

The present invention relates to a system structure capable of performing real-time detection of nucleic acid extraction and amplification reactions and amplified results in a device for implementing a polymerase chain reaction (PCR). A PCR system includes a nucleic acid extraction cartridge configured to extract a nucleic acid of a biological sample via a nucleic acid extraction reagent stored therein and form a PCR preliminary mixture by being additionally mixed with a polymerase reaction dried product, a PCR plate inserted into the nucleic acid extraction cartridge, having a channel coupled to the nucleic acid extraction cartridge, and receives a nucleic acid solution or the PCR preliminary mixture extracted from the nucleic acid extraction cartridge and diversely accommodates a PCR reaction dried product containing a dried primer/probe or a primer/probe in at least one reaction well, a temperature control module disposed above (Continued)

the PCR plate 200 and including a pair of heating blocks 310 and 320 adjacent to the reaction well (W) to apply different temperatures, and a scanning module scanning a concentration of a reactant amplified in the reaction well (W).

18 Claims, 18 Drawing Sheets

(52) U.S. Cl.
CPC ........ *C12Q 1/6806* (2013.01); *B01L 2200/04* (2013.01); *B01L 2200/10* (2013.01); *B01L 2200/147* (2013.01); *B01L 2200/16* (2013.01); *B01L 2300/0627* (2013.01); *B01L 2300/1805* (2013.01); *B01L 2300/1844* (2013.01); *B01L 2300/1894* (2013.01)

(58) Field of Classification Search
CPC ......... B01L 2200/16; B01L 2300/0627; B01L 2300/1805; B01L 2300/1844; B01L 2300/1894; C12Q 1/6806
See application file for complete search history.

(56) References Cited

U.S. PATENT DOCUMENTS

| 2015/0136604 A1 | 5/2015 | Nielsen et al. |
| 2018/0154363 A1 | 6/2018 | Figley et al. |

FOREIGN PATENT DOCUMENTS

| CN | 102203272 A | 9/2011 |
| CN | 205088229 U | 3/2016 |
| CN | 106916743 A | 7/2017 |
| CN | 206828550 U | 1/2018 |
| JP | 2008/200006 A | 9/2008 |
| JP | 2010/078493 A | 4/2010 |
| JP | 2016136973 A | 8/2016 |
| JP | 6206688 B | 10/2017 |
| KR | 10/2012/0044197 | 5/2012 |
| KR | 10/20160067872 | 6/2016 |
| KR | 10/20180112069 | 10/2018 |
| KR | 10/2019/0069302 | 6/2019 |
| RU | 2658599 C1 | 6/2018 |
| WO | WO-01/46688 A1 | 6/2001 |

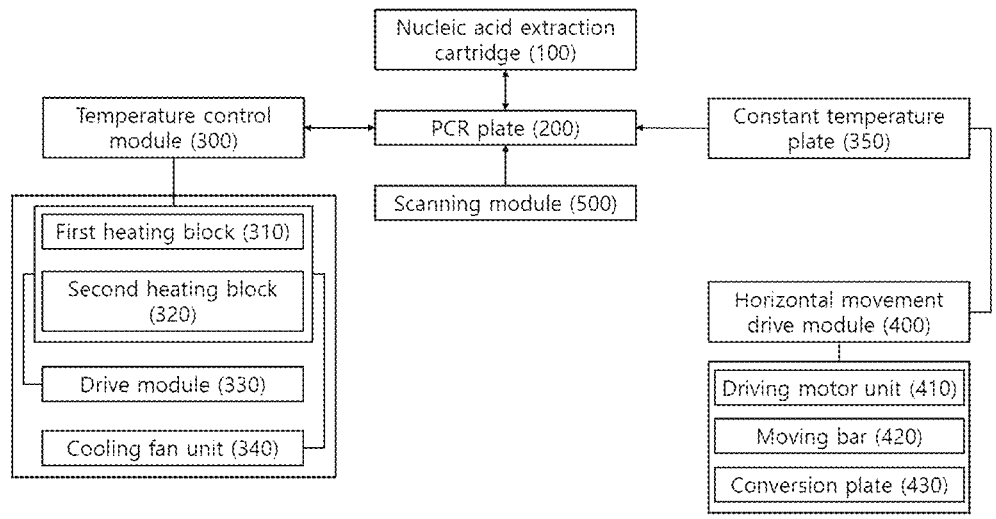
[Fig. 1]
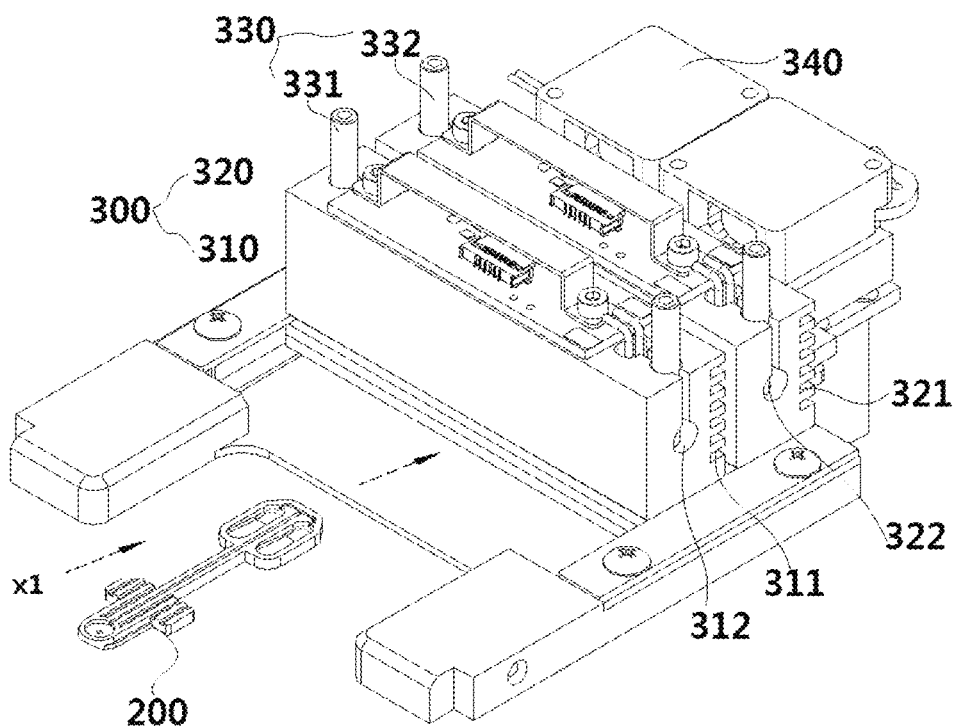
[Fig. 2]

[Fig. 3]
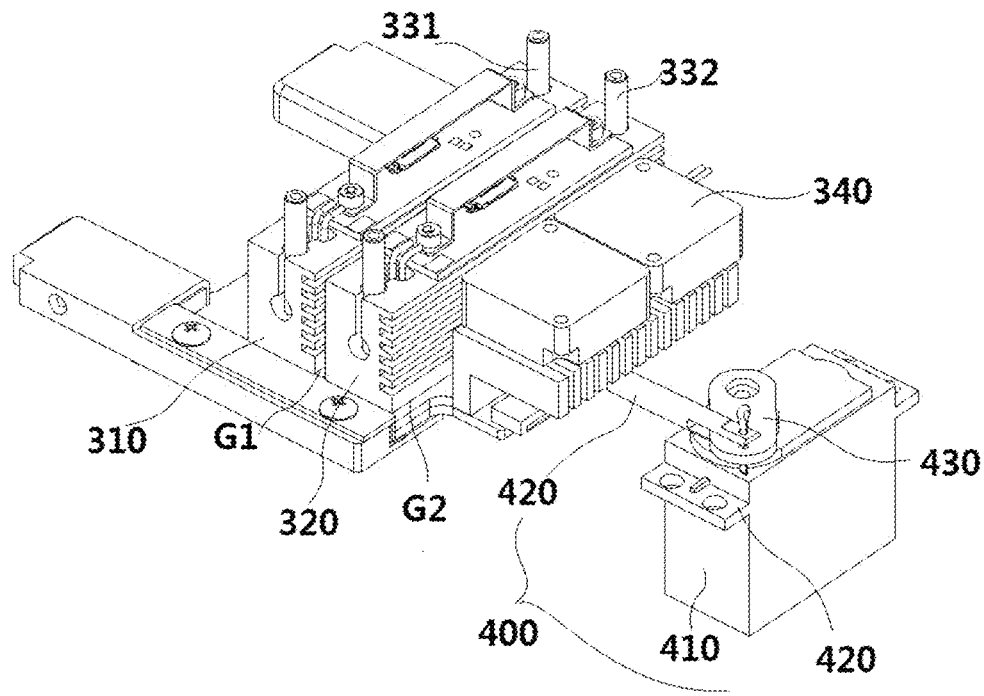
[Fig. 4]
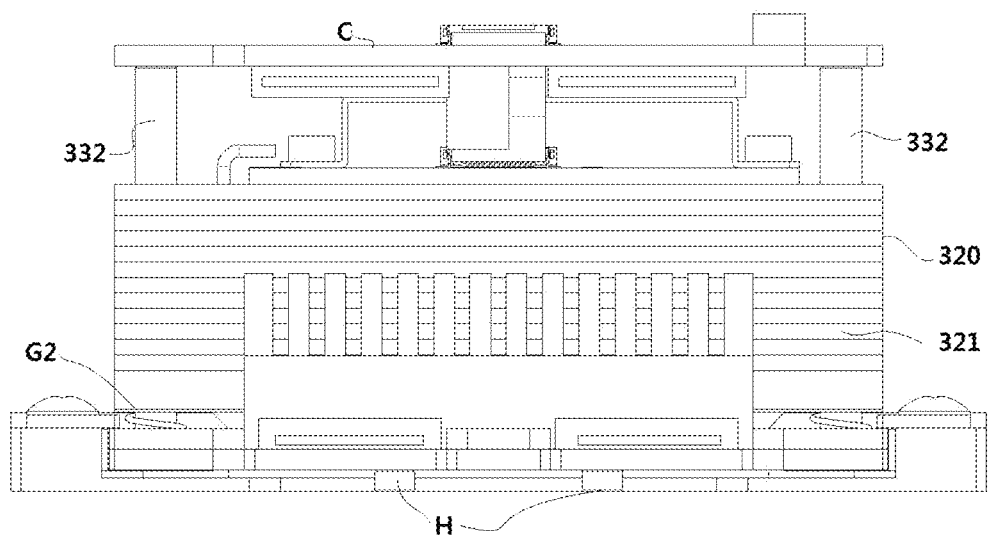

[Fig. 5]
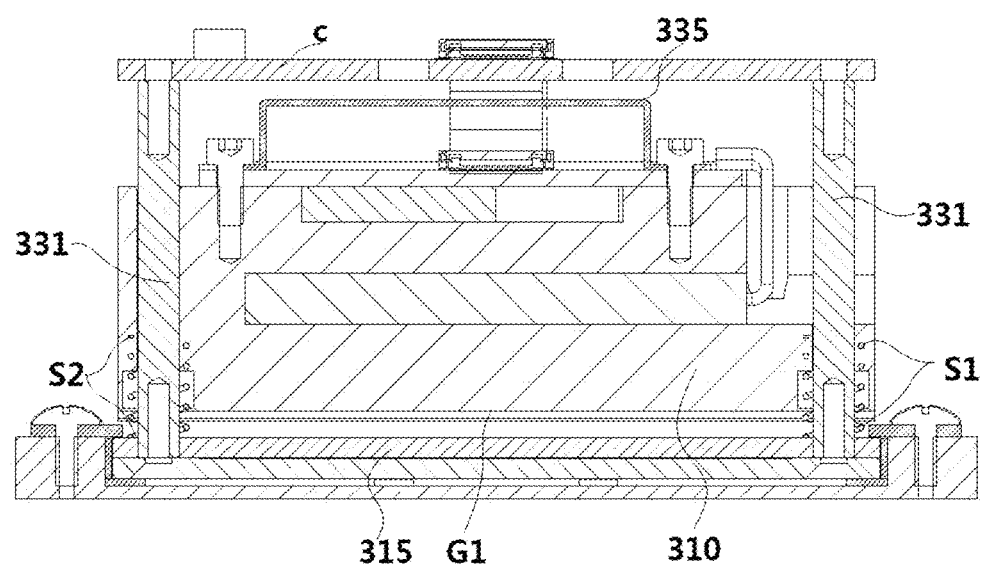

[Fig. 6]
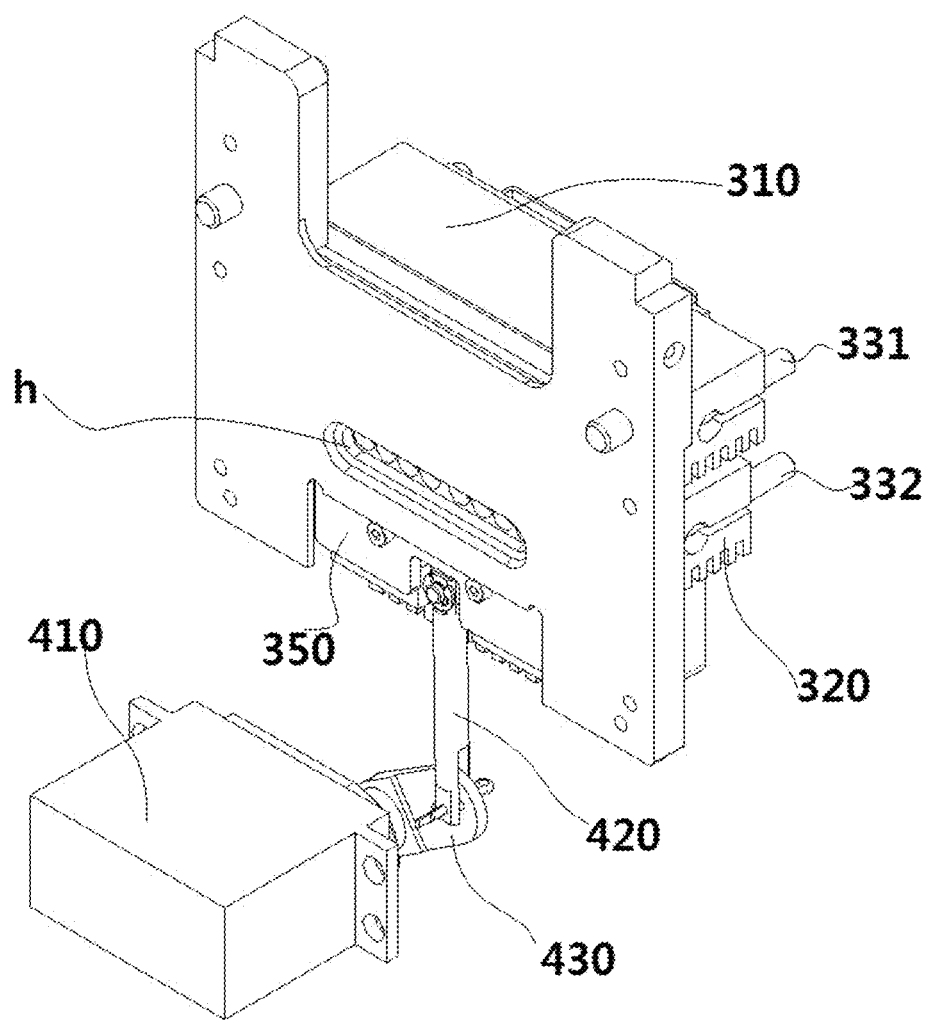

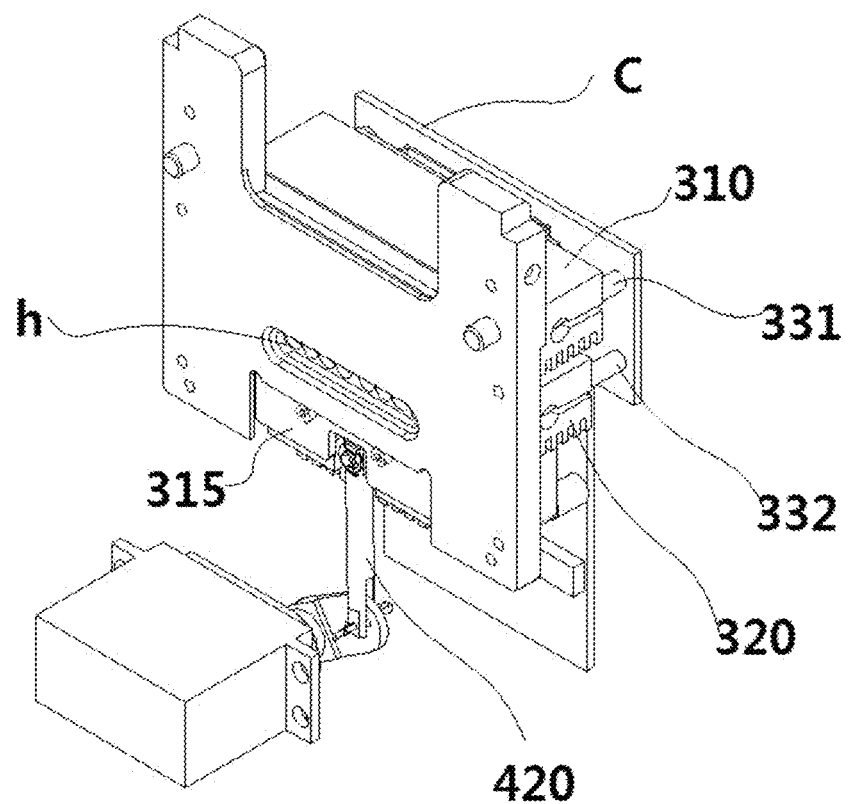
[Fig. 7]

[Fig. 8]
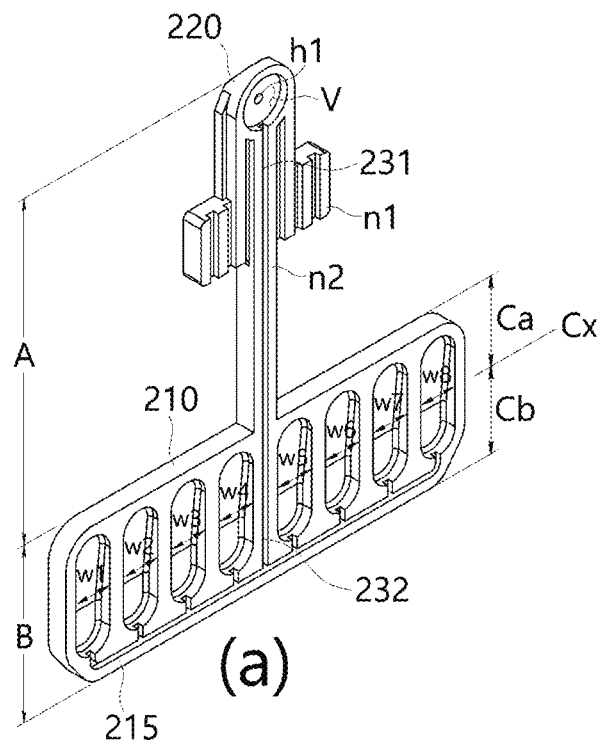
(a)
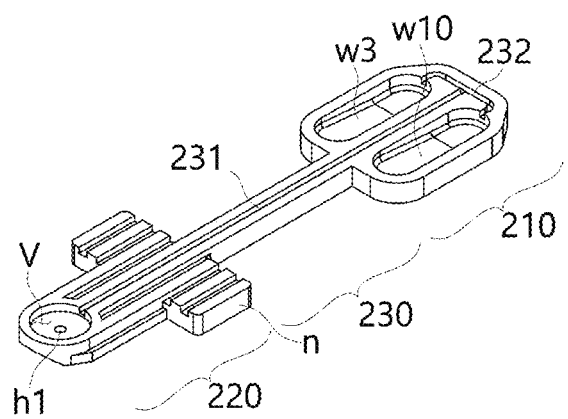
(b)

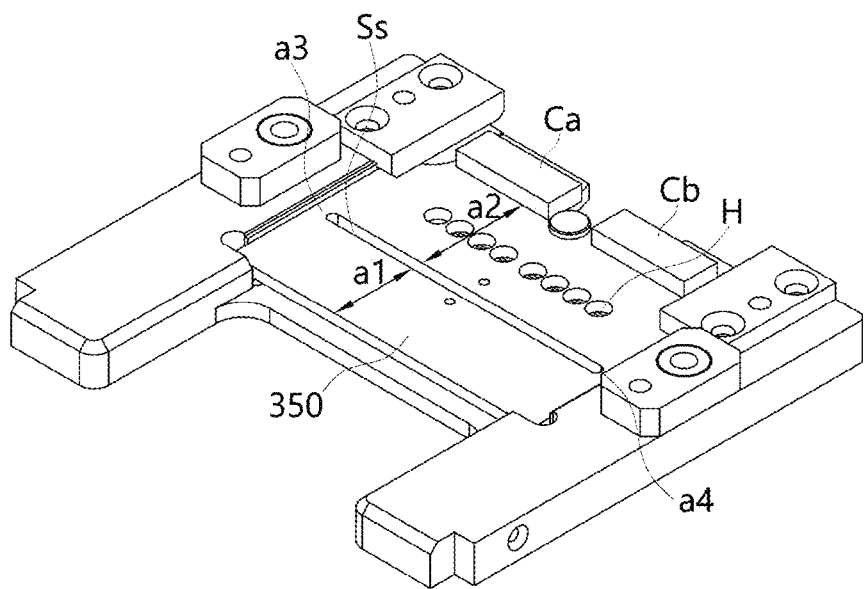
[Fig. 9]

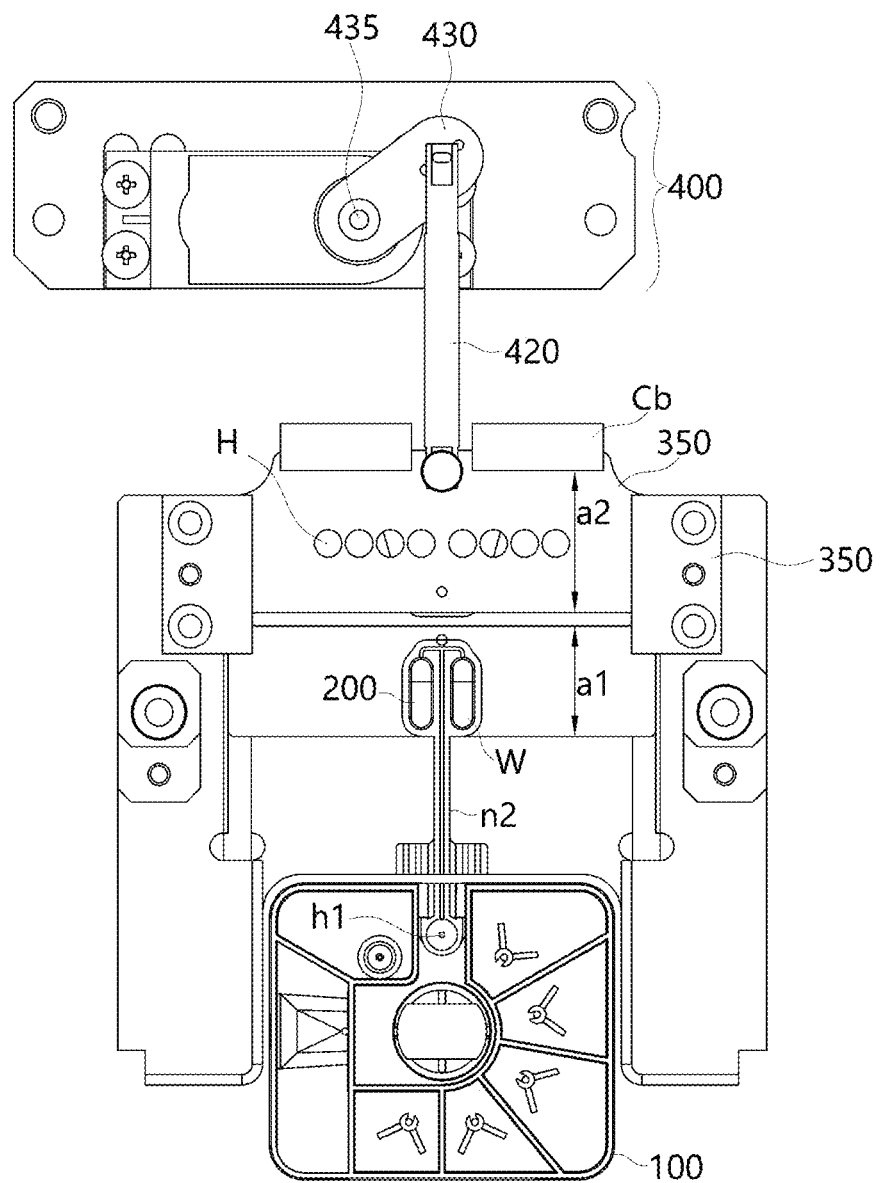
[Fig. 10]

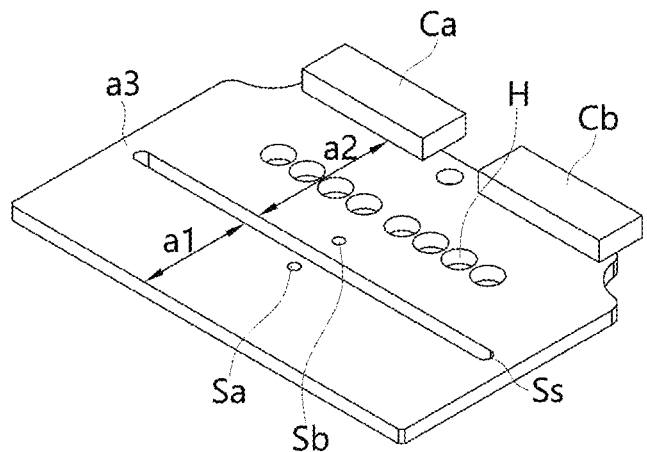
[Fig. 11]
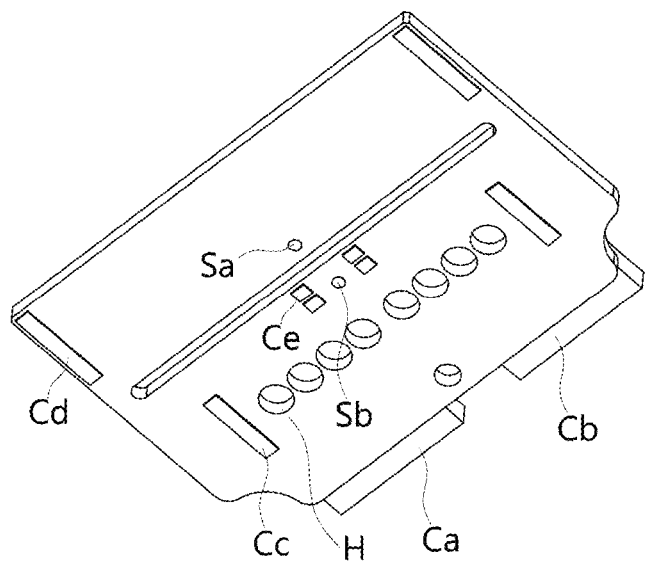
[Fig. 12]

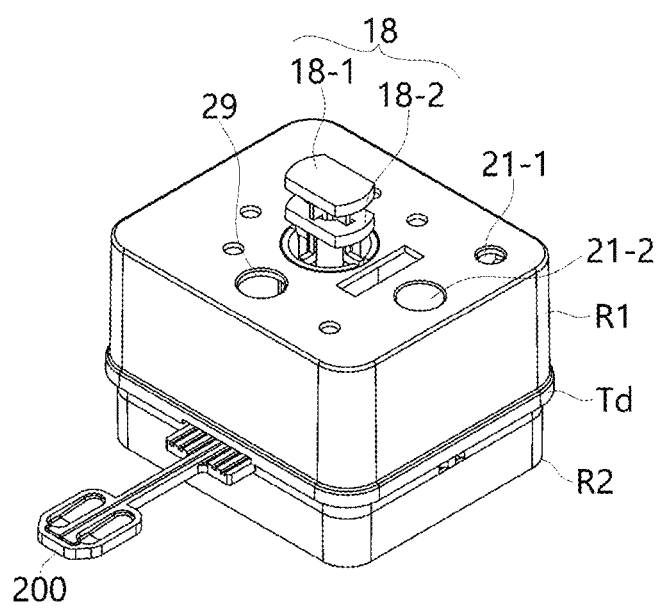
[Fig. 13]

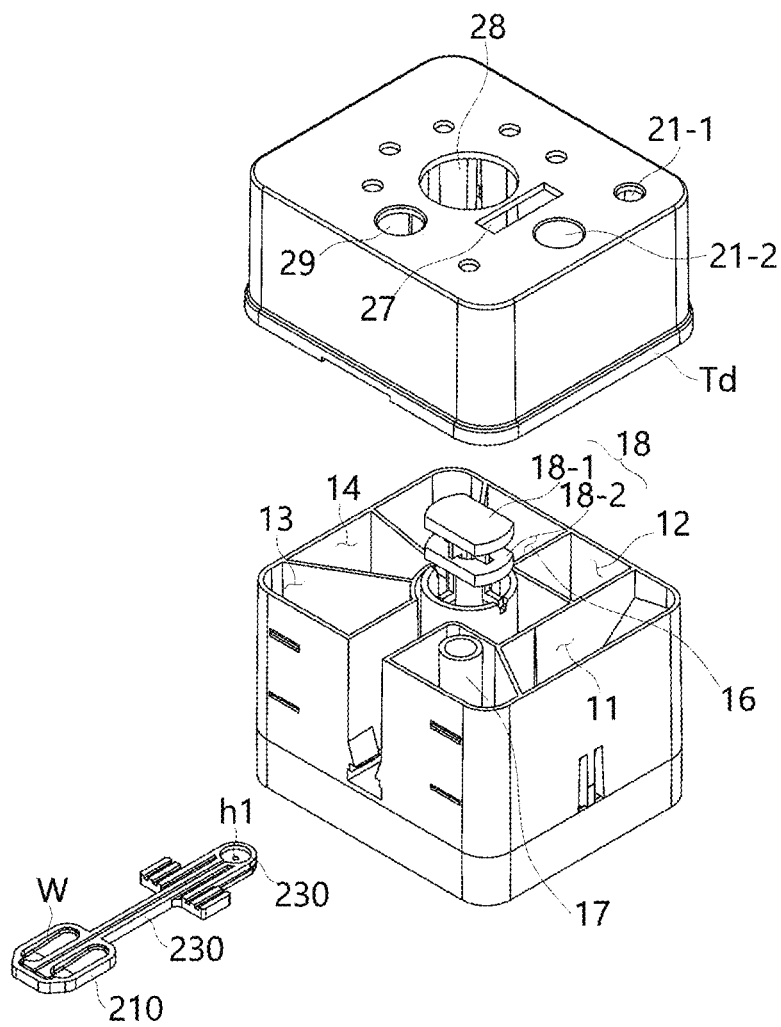
[Fig. 14]

[Fig. 15]
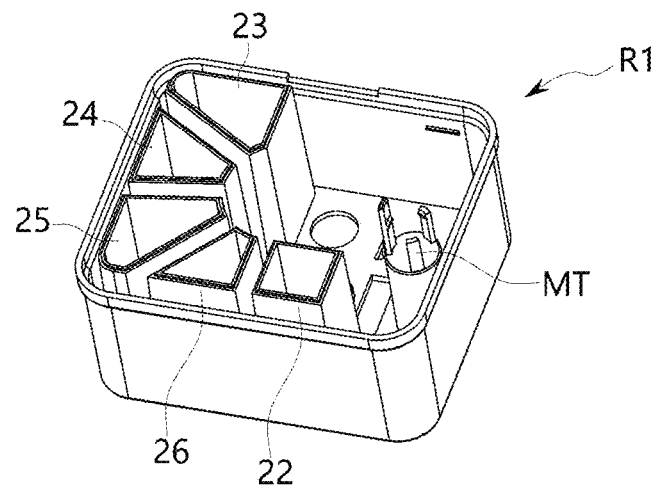
[Fig. 16]
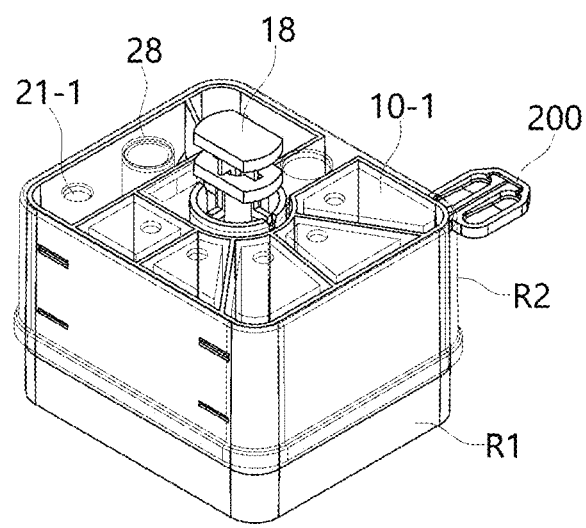

[Fig. 17]
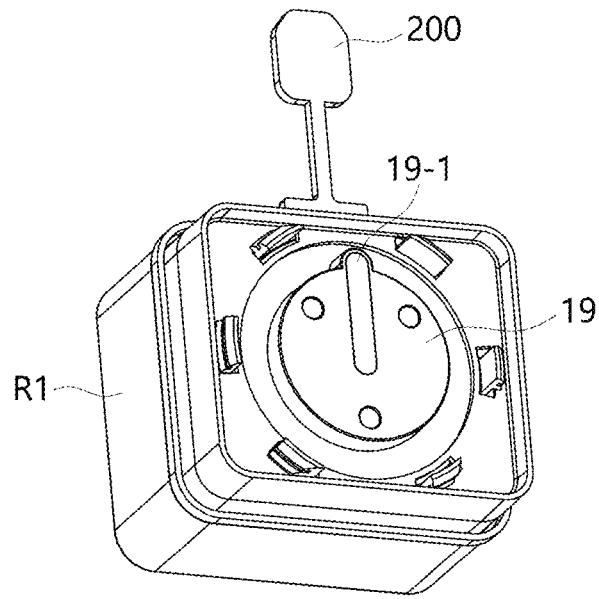
[Fig. 18]
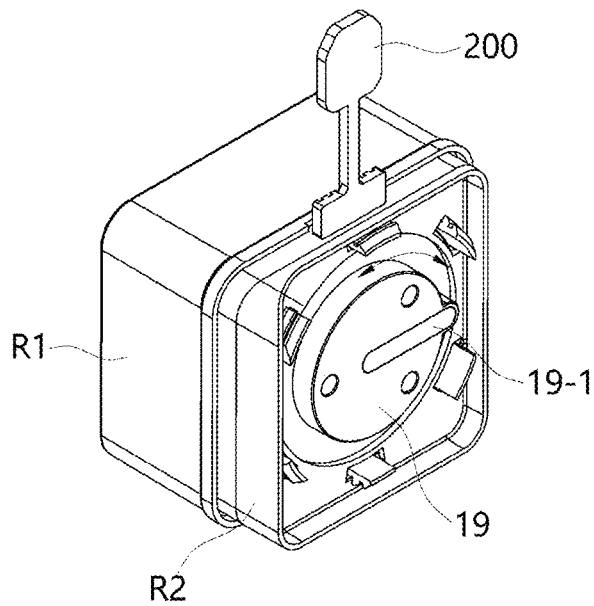

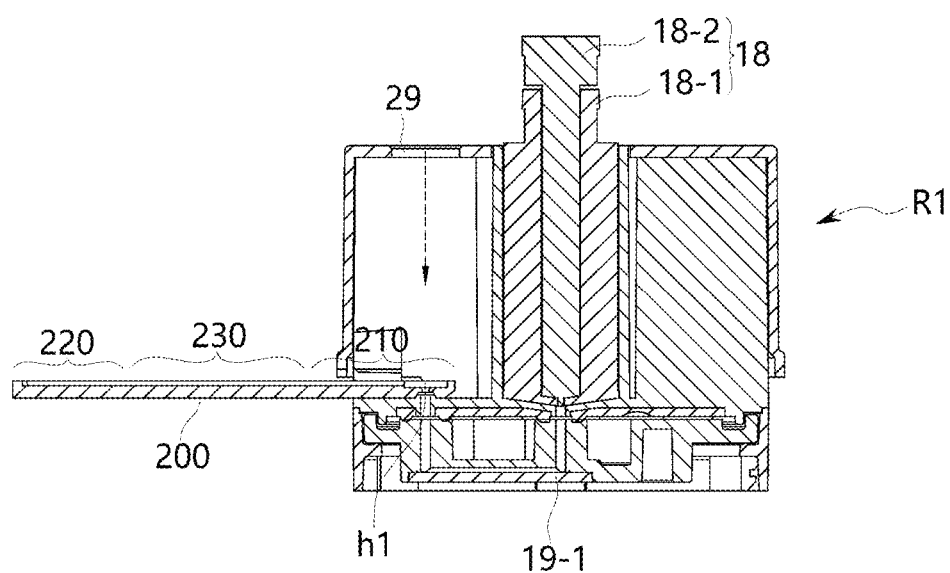
[Fig. 19]

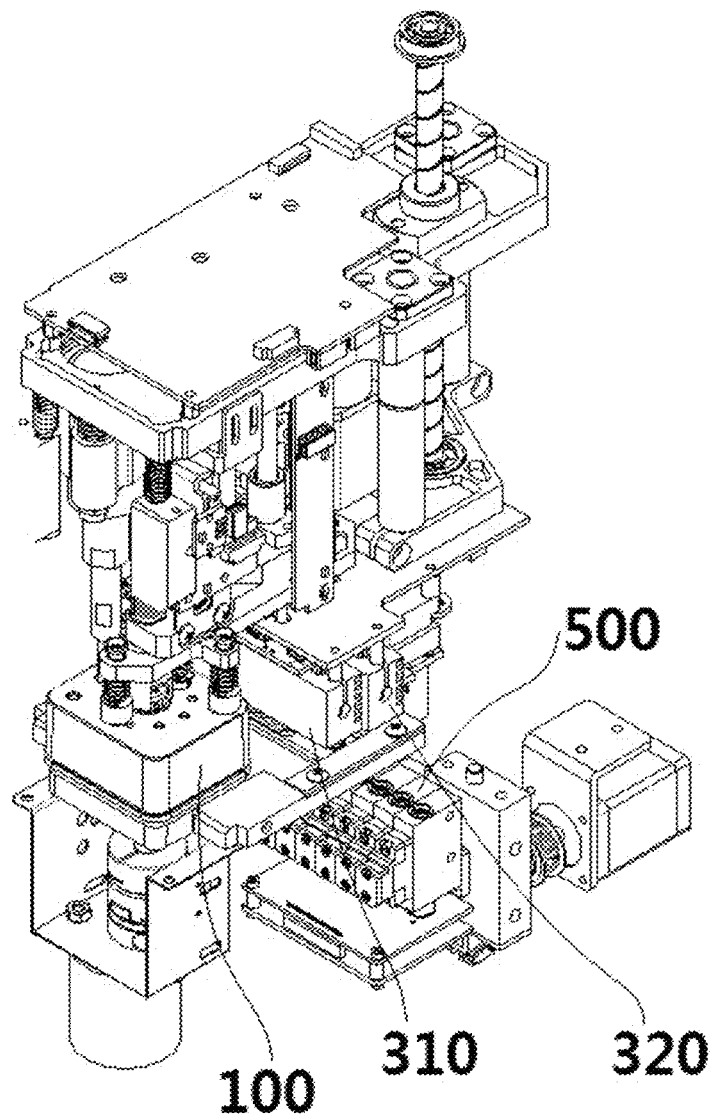
[Fig. 20]

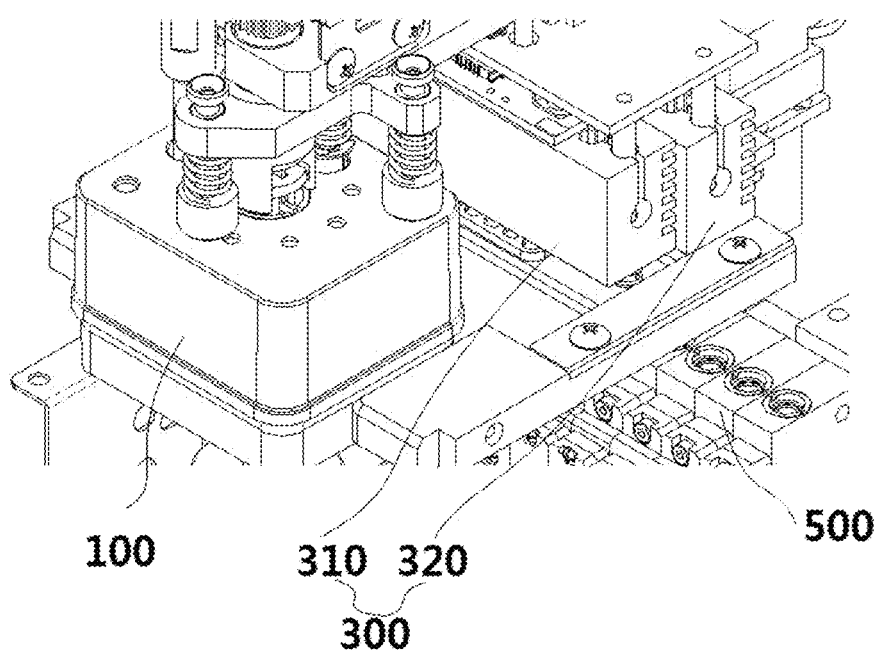
[Fig. 21]

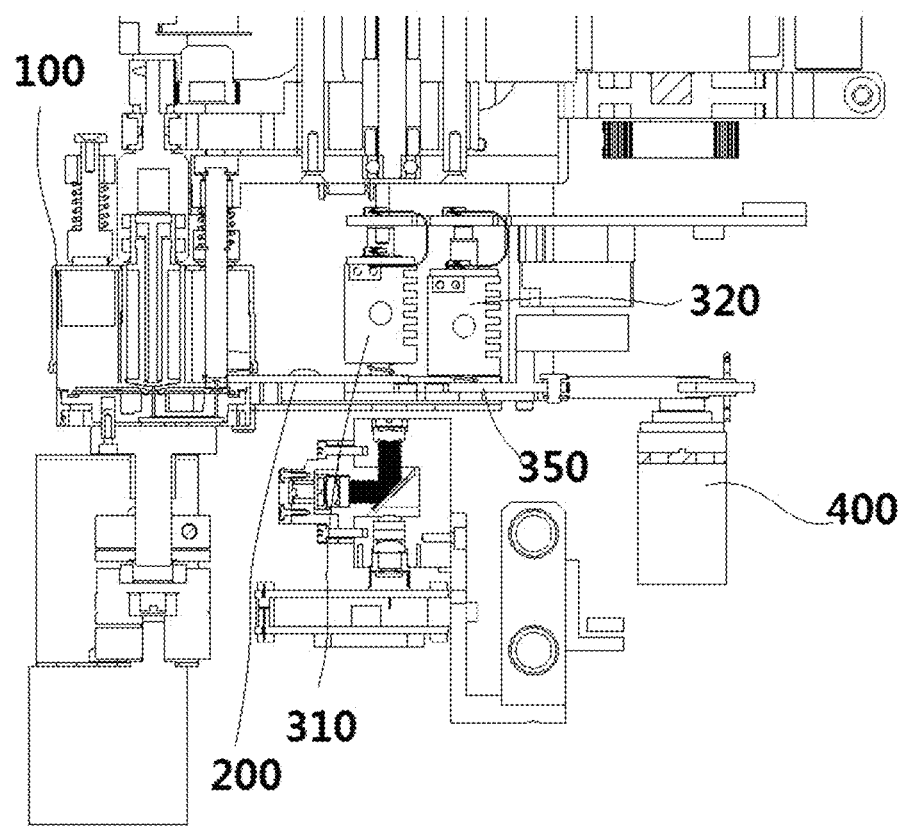
[Fig. 22]

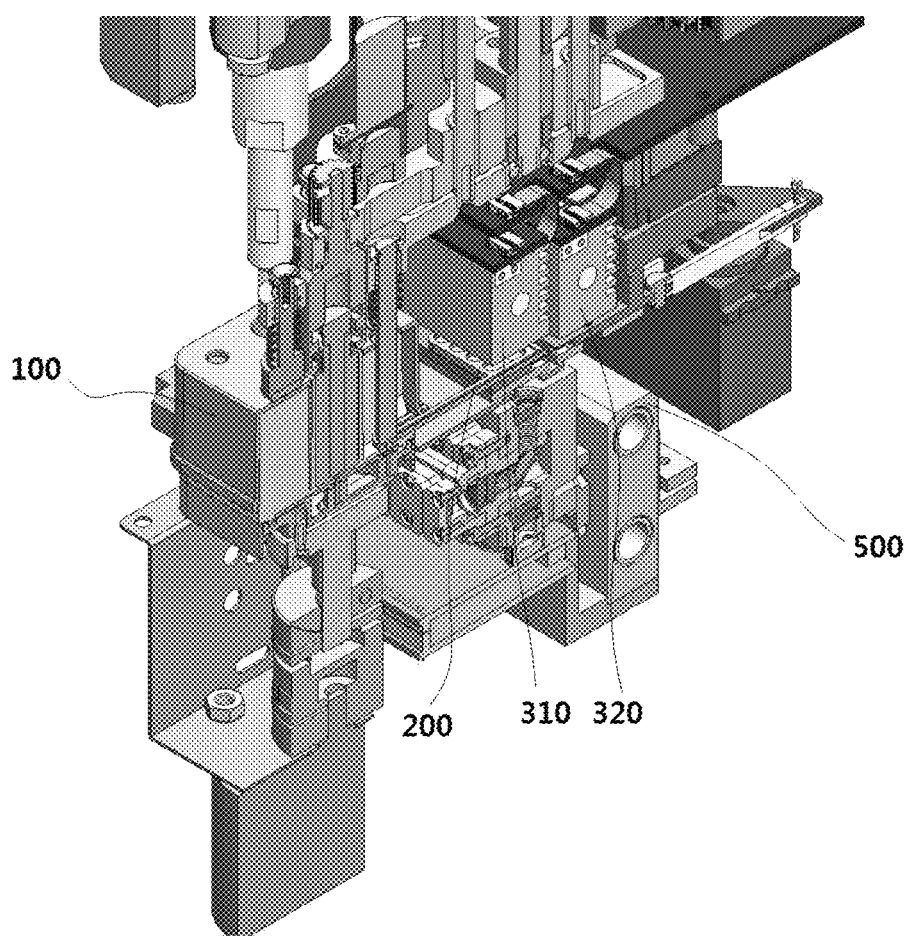
[Fig. 23]

POLYMERASE CHAIN REACTION SYSTEM

CROSS REFERENCE TO RELATED APPLICATIONS

This patent application is the national stage of International Patent Application No. PCT/KR2020/004840, filed on Apr. 9, 2020, which claims the benefit and priority of Korean Patent Application No. 10-2019-0042463, filed on Apr. 11, 2019, the disclosures being incorporated by reference herein in their entirety as part of the present application.

TECHNICAL FIELD

The present invention relates to a system structure capable of performing real-time detection of nucleic acid extraction and amplification reactions and amplified results in a device for implementing a polymerase chain reaction.

BACKGROUND ART

A point of care (POC) diagnostic technology that accurately and quickly diagnoses a patient's disease regardless of time and place is attracting attention as a very important technology of evidence-based precision medicine. Symptom-based on-site diagnosis quickly inspects all infectious pathogens that cause disease symptoms at once on the basis of disease symptoms such as cough, diarrhea, high fever, and genital abnormality, identifies the causative pathogen, and prescribes the best antibiotics and treatments. The symptom-based on-site diagnosis is a core technology for future precision medicine, and many studies are being added to develop the symptom-based on-site diagnosis. The on-site diagnosis technology has the advantage of enabling fast and accurate diagnosis even by non-specialists in the field, such as using a pregnancy test kit to confirm pregnancy and a blood glucose meter that can check blood sugar. Currently, multiple test methods for a molecular diagnostic technology have been developed that can test various pathogens at the same time, and by using these technologies, it is possible to find out an exact cause of an infectious disease and to make an optimal prescription, thereby reducing a patient's recovery period by treating the disease at an early stage. Accordingly, the molecular diagnostic technology is attracting attention as a core technology of future medicine that improves the quality of medical care and reduces medical costs.

However, in the current molecular diagnosis system, it takes more than three hours to confirm a result and should be used by experienced experts. Accordingly, for a point of care (POC) molecular diagnosis required in the field, it is essential to develop an automated small device that can perform a complex nucleic acid extraction process and real-time gene amplification test fully automatically, and it should be easy to operate even without professional personnel.

As a representative molecular diagnostic method, there is a method using a polymerase chain reaction (PCR) (hereinafter, referred to as "PCR"). Since the PCR was invented by Kary Mullis in 1985, the PCR can quickly and easily amplify specific DNA, and thus, the PCR has been widely used in molecular biology and molecular diagnosis. Using PCR/reverse transcription PCR (PCR/RT-PCR), it is possible to check whether specific DNA/RNA is present in a biological sample, and thus it is widely used to diagnose infection with pathogenic microorganisms such as viruses. This PCR/RT-PCR technology has developed into real-time quantitative PCR, and thus, the result can be learned at the same time as the PCR is finished. Therefore, the PCR/RT-PCR technology is used as a standard diagnostic method to monitor treatment effects of human immunodeficiency virus (HIV), hepatitis C virus (HCV), hepatitis B virus (HBV), or the like because it not only greatly reduces the test time by simplifying the test process, but also can accurately quantify the number of pathogens. In addition, the PCR/RT-PCR technology is used as the most important technology for diagnosing diseases because it can test gene expression patterns or genetic mutations related to specific diseases.

In order to perform the PCR, a nucleic acid extraction step of removing substances that inhibit the PCR reaction from a biological sample and extracting pure nucleic acids is required. The nucleic acid extraction process includes multiple steps, requires skilled techniques to manipulate biological samples and extract nucleic acid, and when the nucleic acid extraction process is performed manually, there is a problem of contamination due to an operator error. Therefore, most of the nucleic acid extraction process uses automated nucleic acid extraction equipment for molecular diagnosis.

Since a real-time quantitative PCR device is required for PCR reaction and detection of reaction products, conventionally, molecular diagnosis has been mainly carried out in large hospitals or clinical laboratory specialized institutions.

Through recent research and development, various automated systems and devices using the same have been developed that automate all processes of nucleic acid extraction, PCR reaction, and reaction product detection so that the PCR can be easily used even without specialized skills.

However, there are problems that the existing devices are too expensive or take a lot of processing time, and it is difficult to perform various tests at once.

To explain a basic principle of the PCR, when a DNA double helix is heated to 95° to be separated into single strands, and then a reaction solution is cooled to an annealing temperature so that primers complementary to both ends of a site to be amplified in a PCR reaction solution are selectively hybridized, a reaction is repeatedly performed in which DNA polymerase makes a double helix by sequentially linking four types of A, G, T, and C complementary nucleotide triphosphates to each single strand. The PCR reaction is a reaction in which a specific DNA double helix is exponentially amplified by $2^n$ by repeatedly performing 30 to 45 cycles (n) of experimentally heating and cooling the PCR reaction solution. The RT-PCR reaction was expanded as a method for detecting RNA by synthesizing cDNA through a reverse transcription reaction and then amplifying the synthesized cDNA through PCR.

To explain a principle of the newly developed real-time quantitative PCR, in order for PCR to be used in full-scale for molecular diagnosis, the real-time quantitative PCR is a method for quantitative analysis of amplified DNA using the PCR reaction in which a substance that emits fluorescence in proportion to the amount of DNA is added to the PCR reaction solution, and then fluorescence is measured at each cycle to find a cycle in which a critical fluorescence value is detected, and the initial target nucleic acid concentration is quantitatively measured therefrom.

While various applied technologies have been developed since the invention of PCR, numerous pathogens and disease-related gene sequences are known through a Genome Project, and molecular diagnostics that amplify these disease-related DNA/RNA sequences to be qualitatively and quantitatively diagnosed have been rapidly developed. Since it takes about 2 hours to cycle the temperature in conventional PCR, methods for performing PCR more quickly and accurately for on-site diagnosis have been continuously developed. (Lab Chip, 2016, 16, 3866-3884)

In order to perform the PCR reaction in a short time, a temperature of the reaction solution should be changed rapidly. In addition, in order to amplify only a desired target by an accurate PCR reaction, primers should be designed to specifically attach to the desired target, and an annealing temperature should be precisely controlled in the PCR temperature cycle reaction.

For this purpose, micro-PCR reaction vessels have been developed that have a smaller heat capacity than that of a 0.5 ml or 0.2 ml reactor commonly used in laboratories and better heat transfer. Since these microreactors use a small amount of reaction solution and have a large surface area, heat is transferred quickly, enabling rapid heating and cooling. 10 µl of PCR solution was put into a thin reaction groove of 40 to 80 um with a size of 17×15 mm on a silicon wafer and covered with a glass plate to maintain a high surface area (>100 mm$^2$/10 µl). However, using the conventional Peltier type thermal block, it could not be shown that one cycle shortened the time to about 3 minutes (Clin. Chem. 40/9, 1815-1818 (1994)).

In order to rapidly heat the PCR reactor, a method of repeatedly immersing the PCR reactor in a high-temperature water bath and a low-temperature water bath was developed as an early PCR reaction device. (Turbo Thermalcycler. Bioneer Corp. Daejeon). In the PCR equipment that circulates reactors in zones with different temperatures using a space-moving method, it is possible to allow the PCR reaction to be carried out quickly and accurately by immersing the reactor in a constant temperature water bath where the temperature is accurately maintained in advance. However, in the PCR equipment, several constant temperature baths are required and the equipment is large and maintenance is laborious. Accordingly, PCR equipment adopting a time-difference temperature circulation method that changes the temperature according to time using a Peltier element in a fixed block is predominant.

The PCR method using micro-channels has been also developed as a space movement temperature circulation method and a time difference temperature circulation method. The space movement temperature circulation method can be broadly divided into an open reactor method in which a continuous flow is performed in a First-In-First-Out (FIFO) method and a closed method in which repeated movements are performed in different temperature sections. The open method was developed in 1994 by Nakano et al. by winding a capillary tube around a cylindrical block having compartments with different temperatures and allowing a PCR solution to continuously flow to the capillary tube. (Biosci. Biotech. Biochem., 58(2), 349-352, 1994). In 1998, it was confirmed by Kopp et al. that the PCR was carried out by passing a 10 µl solution through 20 cycles of a 4.5-second cycle using micro-channel PCR equipment that repeatedly flows through high and low temperature sections. (Science 280 1046-1048, 1998)

PRIOR ART LITERATURE

Korean Patent Publication No. 10-2016-0067872

DISCLOSURE

Technical Problem

The present invention is directed to providing a device capable of performing fully automatic target nucleic acid detection through extraction of nucleic acids from a biological sample, polymerase chain reaction (PCR) reaction, and scanning pieces of excitation light in various wavelength bands and fluorescence corresponding to the excitation light, inspecting multiple targets with one operation, being easily used, and obtaining accurate results in a short time.

Further, the present invention is directed to providing a device capable of rapidly and repeatedly applying a temperature required for a denaturation process and an exact temperature needed for annealing to a reaction target in a temperature control process required for a PCR process to perform rapid and correct PCR and maximize reliability of the reaction.

Technical Solution

According to an aspect of the present invention, there is provided a polymerase chain reaction (PCR) system including a nucleic acid extraction cartridge (100) configured to extract a nucleic acid of a biological sample via a nucleic acid extraction reagent stored therein, a PCR plate (200) having a channel coupled to the nucleic acid extraction cartridge and at least one reaction well (W) which accommodates a PCR dried mixture containing a primer, a primer/probe, or a primer probe and receives a nucleic acid solution extracted from the nucleic acid extraction cartridge (100); and a temperature control module (300) disposed above the PCR plate (200), adjacent to the reaction well (W) to apply different temperatures, and having a pair of heating blocks (310, 320) that are movable horizontally and vertically.

Advantageous Effects

According to embodiments of the present invention, it is possible to provide a device capable of automatically performing real-time reaction production detection through extraction of nucleic acids from a biological sample, polymerase chain reaction (PCR) reaction, and scanning pieces of excitation light in various wavelength bands and fluorescence corresponding to the excitation light, inspecting multiple targets with one operation, being easily used, and obtaining accurate results in a short time.

In addition, according to embodiments of the present invention, a temperature control required for the PCR process and an accurate temperature required for a denaturation step and coupling can be quickly applied in real-time to a reaction target at once so that accurate PCR is possible, and it is possible to maximize reliability of the reaction.

That is, in a case of the conventional temperature control method of moving a reaction solution and increasing the temperature, it is not possible to apply a uniform increase in temperature, which is disadvantageous for the PCR reaction. That is, it is not possible to achieve temperature uniformity in the entire reactant at the same time according to a method of moving the reaction solution and sequentially increasing the temperature, and thus, other reactions are highly likely to occur. However, in the embodiment of the present invention, it is possible to remove the above-described problems, maintain a temperature range set in the heating block at a constant temperature, and more effectively increase the temperature required for the PCR reaction by directly pressurizing the entire reaction solution to increase the temperature.

Furthermore, in order to minimize a time delay in the process of changing a temperature from a high temperature to a low temperature, the block-shaped heating block structures are arranged to be spaced apart side by side. Therefore, when the PCR plate is pressurized, the positions of the heating blocks are changed so that the heating blocks having individually different temperatures are pressurized in real time, and thus, problems caused by delay in the time required in the process of temperature change can be innovatively solved.

Furthermore, the PCR plate is implemented to be insertable into the nucleic acid extraction cartridge, the nucleic acid extraction cartridge is commonly used and the PCR plate used in various test kits is stored in a small space, and the PCR plate suitable for testing can be inserted and used as needed. A maximum of six fluorescence values can be analyzed in one reaction well provided in the PCR plate, and the number of reaction wells in the PCR plate can be increased to eight if necessary. Therefore, it is possible to amplify and detect all pathogens that may be included in a patient's biological sample related to symptoms and perform symptom-based multi-molecular diagnostic testing.

In addition, according to one embodiment of the present invention, the constant temperature plate is divided into regions having the gradient of the first temperature and the second temperature. Accordingly, when the heating block is pressurized through the drive module, the region having a set temperature (first temperature or second temperature) corresponding to the temperature of the heating block is correspondingly moved, contact pressurization is simultaneously performed on the upper and lower surfaces of the PCR plate, and thus, it is possible to obtain double efficiency compared to a constant temperature plate method maintained at a single temperature.

In addition, by implementing a movable constant temperature plate structure, a sliding tape is used as a configuration for performing a driving operation to ensure reliability of a configuration and movement of a product. Moreover, the heating of the plate contained in the target is implemented simultaneously on the upper and lower surfaces of the plate, and thus, the inspection time can be reduced by half.

DESCRIPTION OF DRAWINGS

FIG. 1 is a block diagram illustrating main components constituting a polymerase chain reaction (PCR) system according to one embodiment of the present invention.

FIGS. 2 to 7 are views for describing a structure of a temperature control module (300) in the present invention.

FIG. 8 illustrates one embodiment of a PCR plate (200) applied to the present invention.

FIGS. 9 to 12 are conceptual views for describing structures and operations of a constant temperature plate and a horizontal movement drive module applied to the present invention.

FIG. 13 is a perspective view of a nucleic acid extraction cartridge of the present invention and illustrates a structure in which the above-described PCR plate is inserted and coupled.

FIG. 14 is an exploded perspective view of FIG. 13.

FIG. 15 illustrates an internal structure of a cartridge cover portion (R1) in the structure of FIG. 14.

FIG. 16 is a perspective view illustrating a coupling state of the structure of FIG. 14.

FIGS. 17 to 19 illustrate lower portion operating states of the cartridge structure of the present invention.

FIG. 20 illustrates an overall structure and layout of a device constituting the above-described PCR system of the present invention.

FIG. 21 is an enlarged view of a coupling arrangement of main portions of the present invention in FIG. 20, and FIG. 22 is a conceptual view of a vertical section of portions of FIG. 21 for describing the arrangement of the main components.

FIG. 23 is a lateral perspective cross-sectional conceptual view of FIG. 22.

MODES OF THE INVENTION

Advantages and features of the present invention and methods for achieving them will become apparent with reference to the embodiments described below in detail in conjunction with the accompanying drawings. However, the present invention is not limited to the embodiments described herein and may be embodied in other forms. Rather, the embodiments introduced herein are provided so that the disclosed subject matter may be thorough and complete and so that the spirit of the present invention may be sufficiently conveyed to those skilled in the art.

The terms used in the present application are only used to describe specific embodiments and are not intended to limit the present invention. The singular expression includes the plural expression unless the context clearly dictates otherwise. In the present application, terms such as "comprise" or "have" are intended to designate that a feature, number, step, operation, component, part, or combination thereof described in the specification is present. That is, it should be understood that the terms such as "comprise" or "have" do not preclude the possibility of addition or existence of one or more other features or numbers, steps, operations, components, parts, or combinations thereof.

FIG. 1 is a block diagram illustrating main components constituting a polymerase chain reaction (PCR) system (hereinafter, referred to as "the present invention") according to one embodiment of the present invention.

Referring to FIG. 1, the PCR system (hereinafter referred to as "the present invention") according to one embodiment of the present invention includes a temperature control module implemented as a heating block structure which is in contact with a PCR reaction plate to apply a specific temperature. The temperature control module can rapidly and repeatedly apply a temperature required for a denaturation process and an exact temperature required for annealing to a reaction target at once in real time without a time difference in a temperature control process required for a PCR process to perform rapid and correct PCR and maximize reliability of the reaction.

In the temperature control module according to the present invention, in order to minimize delay in a time required from a first temperature to a relatively low second temperature or from a second temperature to a relatively high first temperature in the reverse process, by changing the positions of the heating blocks set to the first temperature and the second temperature, the PCR reaction plate is pressurized in real time, and thus, it is possible to innovatively solve a problem caused by the time delay required in a temperature change process.

Furthermore, the present invention may further include a constant temperature plate structure that is disposed below the PCR plate and operates as a horizontally moving structure in a sliding manner. In this case, the constant temperature plate structure that maintains the temperature of the PCR plate at the first temperature or the second temperature minimizes the time required to apply the temperature change condition to maximize a reaction rate.

Specifically, the present invention may include a nucleic acid extraction cartridge 100 configured to extract a nucleic acid of a biological sample via a nucleic acid extraction reagent stored therein and form a PCR preliminary mixture or template, a PCR plate 200 inserted into the nucleic acid extraction cartridge, having a channel coupled to the nucleic acid extraction cartridge, and accommodated in at least one reaction well which receives the PCR preliminary mixture or template extracted from the nucleic acid extraction cartridge 100 and accommodates a PCR dried product containing a primer, a primer/probe, or a primer probe, and a temperature control module 300 disposed above the PCR plate 200 and including a pair of heating blocks 310 and 320 adjacent to the reaction well W to apply different temperatures.

According to the above configuration of the present invention, even non-professionals can conveniently input a desired sample through the nucleic acid extraction cartridge so that nucleic acid extraction can be performed freely. Moreover, by using the heating block structure that can directly apply a target temperature to the reaction solution in the PCR plate through a thin film and compression, fast and precise temperature control of a temperature cycle required for amplification applied to the PCR plate 200 can be performed.

Moreover, it is possible to provide a PCR device implemented as one system which can detect reactants by scanning pieces of excitation light in various wavelength bands and fluorescence corresponding to the excitation light below the PCR plate in real time through a scanning module.

FIGS. 2 to 7 are views for describing the structure of the temperature control module 300 in the present invention.

FIGS. 2 and 3 are perspective views illustrating the temperature control module of the present invention.

Referring to FIGS. 2 and 3, the temperature control module 300 performs constant temperature control on the PCR plate 200 which extracts a nucleic acid of a biological sample, mixes the nucleic acid with a polymerase, and receives a PCR preliminary mixture or nucleic acid extract from a nucleic acid extraction cartridge.

Specifically, the temperature control module 300 includes a first heating block 310 which includes a first pressing surface G1 corresponding to a surface of a reaction well W implemented in the PCR plate 200 and is maintained at a set temperature within a range of a temperature (hereinafter, referred to a "first temperature") required for denaturation by a heating unit. Moreover, the temperature control module 300 includes a second heating block 320 which is disposed at a position corresponding to the first heating block 310 and spaced apart from the first heating block 310, includes a second pressing surface G2 corresponding to the surface of the reaction well, and is maintained at a temperature set to a range of a temperature (hereinafter, referred to a "second temperature) required for annealing by the heating unit. In particular, structures of the first heating block 310 and the second heating block 320 may be implemented to enable horizontal movement and vertical movement.

In an exemplary embodiment, each of the first heating block 310 and the second heating block 320 may have a three-dimensional structure and include a flat pressing surface on a lower surface thereof. Moreover, the first heating block 310 and the second heating block 320 may be disposed to be spaced apart from each other and have a temperature in a different temperature range.

Specifically, as illustrated in FIGS. 2 and 3, the first heating block 310 and the second heating block 320 may have a structure of being disposed to face each other. Moreover, an upper surface of each of the first heating block 310 and the second heating block 320 may be implemented to have a flat structure capable of performing a pressurization function, and a three-dimensional structure such as a cuboid may be provided above the upper surface. The three-dimensional structure such as a cuboid is one embodiment, and as long as a structure has a flat surface for the pressurization, any three-dimensional shape may be included in the gist of the present invention.

In addition, the first heating block 310 and the second heating block 320 may be arranged laterally, adjacent surfaces thereof may be spaced apart from each other, and the first heating block 310 and the second heating block 320 may be maintained to have a different set temperature.

For example, the first temperature of the first heating block 310 is a temperature applied to denaturation which separates double-stranded DNA (including DNA extracted from a biological sample) and may be set in the range of 94 to 96° C. In an exemplary embodiment of the present invention, the first temperature may be maintained at 95° C.

Furthermore, the second temperature of the second heating block 320 is a temperature required for primer annealing to bind a primer to an isolated template DNA and may be set in the range of 50 to 65° C. In an exemplary embodiment of the present invention, the second temperature may be maintained at 55° C.

The first heating block 310 and the second heating block 320 do not contain water or a heat transfer fluid therein but are implemented in a structure having a metal body having a large heat capacity and high heat transfer efficiency. Therefore, the first heating block 310 and the second heating block 320 can be always maintained at the set temperature by the heating unit provided therein. To this end, the heating unit should be controlled through temperature control so that a constant temperature can be maintained by mounting a temperature sensor therein.

That is, in a case where the PCR preliminary mixture is injected into the PCR plate 200, the first heating block 310 moves horizontally to be adjacent to the surface of the PCR plate 200 when the application of the first temperature is required. That is, since the first pressing surface G1 has a flat plate structure, it is possible to simultaneously heat the entire surface of the PCR plate 200 at the same temperature and with the same pressing force, and thus, uniform temperature transfer to the entire sample is possible.

In addition, when it is necessary to apply the second temperature required for a bonding step, the second heating block 320 moves horizontally and is positioned above the PCR plate, and thus, it is possible to simultaneously heat the entire surface of the PCR plate 200 at the same temperature and with the same pressing force.

That is, an additional time is not required to prepare the set temperature reaction, and it is driven in such a way that the entire surface of the PCR plate 200 can be simultaneously heated at the same temperature and with the same pressing force by a simple horizontal operation. Accordingly, compared to the existing method for controlling the set temperature, it is possible to derive a faster and more precise PCR reaction.

In addition, a cooling fan unit 340 capable of implementing a cooling effect may be provided in a space spaced apart between the first heating block 310 and the second heating block 320 so that the first heating block 310 and the second heating block 320 are set to different temperatures and the second heating block can be constantly heated by the first heating block by radiant heat and conductive heat.

It is important that the second heating block 320 is relatively maintained at the second temperature, for example, an annealing temperature of 55° C. To this end, a divergent cooling pattern capable of minimizing thermal interference of the first heating block 310 and easily dissipating excess heat using the cooling fan unit may be provided on the upper portion. As an example of this, in the present invention, the second heating block 320 may further include a temperature control pattern portion 321 implemented on a side portion of the second pressing surface G2. The temperature control pattern portion 321 has a structure in which a plurality of protruding patterns are implemented on the upper portion, and thus, it is possible to increase heat dissipation efficiency by increasing a contact surface area with air, which is advantageous in maintaining a constant low temperature.

Unlike the method of moving the reaction sample implementing the PCR reaction or moving the reaction sample to another heating zone through time setting, according to the present invention described above, the heating block structure is applied so that the temperature can uniformly increase at the same time at the upper portion in a state in which the reaction sample is fixed, and thus, accurate transmission of the first temperature and the second temperature can be realized.

In addition, in the present invention, preferably, the first heating block 310 or the second heating block 320 is interlocked with the drive module 330 that implements the horizontal movement or the vertical movement. The drive module 330 includes guide members 331 and 332 passing through the first heating block 310 and the second heating block 320, and the first heating block 310 and the second heating block 320 can move vertically along the guide members 331 and 332.

That is, in the present invention, the first heating block 310 and the second heating block 320 are disposed to be spaced apart from each other and cross each other according to the operation of the drive module 330 to realize the vertical movement. Furthermore, preferably, elastic members S1 and S2 disposed below the guide members 331 and 332 are further provided, and thus, when the heating block pressurizes the PCR plate, an appropriate elastic force is provided to realize buffering (see FIG. 5).

In addition, in one embodiment of the present invention, a constant temperature plate 350 interlocking with the above-described temperature control module may be further provided.

In addition, in one embodiment of the present invention, a constant temperature plate 350 interlocking with the above-described temperature control module may be further provided.

As illustrated in FIGS. 2 and 3, the constant temperature plate 350 is disposed below the structures of the heating blocks 310 and 320 constituting the temperature control module 300, and after the PCR plate 200 enters, in a case where the first heating block 310 or the second heating block 320 of the temperature control module 300 moves horizontally and vertically to pressurize the PCR plate at the upper portion, the constant temperature plate 350 may have the same temperature as those of the first heating block 310 or the second heating block 320.

To this end, the constant temperature plate 350 may further include a horizontal movement drive module 400 that moves horizontally to a lower portion of the PCR plate 200.

To this end, the constant temperature plate 350 may further include a horizontal movement drive module 400 that moves horizontally to a lower portion of the PCR plate 200.

As illustrated in FIGS. 2 and 3, the horizontal movement drive module 400 may include a moving bar 420 and a driving motor unit 410 coupled to one end of the constant temperature plate 350, and a conversion plate 430 that converts a rotational force of the driving motor unit 410 to a horizontal movement force of the moving bar 420.

This horizontal movement drive module 400 allows the constant temperature plate 350 to be horizontally moved in a downward direction of the temperature control module 300 described above. In particular, the constant temperature plate 350 according to the embodiment of the present invention may be partitioned into a first region heated to a first temperature and a second region which is spaced apart from the first region and heated to a second temperature (refer to descriptions of FIGS. 21 to 23).

In particular, in an exemplary embodiment of the present invention, the temperature control module 300 and the constant temperature plate 350 may be integrated with each other via the guide members 331 and 332.

That is, when the horizontal movement drive module 400 is driven, the temperature control module 300 including the constant temperature plate 350 and the heating blocks 310 and 320 may be moved together.

In this case, the constant temperature plate 350 includes the first region heated to the first temperature and a second region which is spaced apart from the first region and heated to the second temperature, the first pressing surface G1 of the first heating block 310 is disposed to correspond to the upper portion of the first region, and the PCR plate 200 is disposed between the constant temperature plate 350 and the heating blocks 310 and 320 from top to bottom so that the pressurization can be achieved at the same temperature at the same time.

That is, in the embodiment of the present invention, the constant temperature plate 350 is divided into regions having a gradient of the first temperature and the second temperature. Accordingly, when the heating block is pressurized through the horizontal movement drive module 400, the region having a set temperature (first temperature or second temperature) corresponding to the temperature of the heating block is horizontally moved to slide correspondingly, contact pressurization is simultaneously performed on the upper and lower surfaces of the PCR plate, and thus, it is possible to obtain double efficiency compared to a constant temperature plate method maintained at a single temperature.

FIG. 4 is a cross-sectional view of the temperature control module in FIG. 3 viewed from the rear, and FIG. 5 is a cross-sectional view of the temperature control module viewed from the front.

As described above, the temperature control module 300 of the present invention includes the drive module 330 that implements the horizontal movement or the vertical movement of the first heating block 310 and the second heating block 320 so that the operation of the heating module can be automated.

Referring to FIGS. 2 to 5, the drive module 330 performs the operation of vertically moving the first heating block 310 and the second heating block 320, and at the same time the horizontal movement drive module 400 moves the first heating block 310 and the second heating block 320 horizontally so that the portion in contact with the surface of the reaction well on the PCR plate 200 can be changed to the first pressing surface G1 or the second pressing surface G2.

The first heating block 310 and the second heating block 320 are disposed side by side in a state of being spaced apart from each other, guide grooves 312 and 322 (see FIG. 2) are provided to pass through the first heating block 310 and the second heating block 320, and the first heating block 310 and the second heating block 320 are seated on the guide members 331 and 332 passing through the guide groove. Accordingly, the first heating block 310 and the second heating block 320 perform vertical movement along the guide members 331 and 332, and the PCR plate can be pressurized from the top.

Of course, in this case, the constant temperature plate 350 is disposed below the first heating block 310 and the second heating block 320, the heating blocks including the regions having the same temperatures as the first temperature and the second temperature correspond to the constant temperature plate 350, and thus, the PCR plate can be pressurized from top and bottom.

As described above, according to the temperature control module 300 in the present invention, in the entire PCR target in the PCR plate 200, the first temperature and the second temperature can be directly applied to the entire PCR plate surface, and thus, it is possible to realize excellent effects in terms of application speed and reaction efficiency.

In addition, the structure of the heating block of the temperature control module 300 is located at the upper portion where the horizontal movement is possible at any time and is lowered only when being pressurized with the PCR plate.

In order to implement such a structure, a first elastic member S1 may be provided which is inserted into the driving frame and has a restoring force to always rise upward when not being pressurized. In the present invention, a second elastic member 335 that transmits a pressing force to prevent excessive application of pressing force is provided when implementing pressing in contact with the PCR plate 200 (see FIG. 5). The second elastic member 335 is implemented as a plate spring structure in the illustrated embodiment and exerts a constant buffering force when the first and second heating blocks are pressurized in the downward direction so that excessive pressing force is not applied to the surface of the PCR plate.

In addition, in the system structure of the present invention, the PCR plate 200 has a plate-shaped structure in which a reaction well is implemented on the upper surface. In this case, the PCR plate 200 is configured to further include the structure of the constant temperature plate 350 at the bottom to maintain a constant temperature, for example, the second temperature (for example, 55° C.) range.

This is because when the temperature is increased by the temperature control module 300 of the present invention being pressed against the first heating block of the first temperature (for example, 95° C.) or when the temperature is increased by the temperature control module 300 of the present invention being pressed against the second heating block of the second temperature (for example, 55° C.), internal amplification efficiency is much better only when the PCR plate 200 reaches the target temperature quickly.

Therefore, in one embodiment of the present invention, preferably, the constant temperature plate 350 is further provided which is disposed below the PCR plate 200 and maintains the temperature of the PCR plate 200 at the second temperature.

In particular, it is preferable that the structure of the constant temperature plate 350 is mounted in a fixed manner and implemented so that a constant set temperature is applied. However, as described above, it is more preferable that the constant temperature plate 350 is divided into the regions which apply the first temperature and the second temperature, and the constant temperature plate can move horizontally.

FIG. 6 is a view illustrating a state in which the constant temperature plate 350 is horizontally moved to the lower portion of the temperature control module through the horizontal movement drive module 400 in the structure of FIG. 2 and entered, and FIG. 7 illustrates a state where the constant temperature plate in the operation of FIG. 6 is horizontally moved outward to change the temperature region.

That is, in the structure of FIG. 6, when the first heating block 310 is disposed to apply the first temperature, the first region in the constant temperature plate 350 is horizontally moved to the lower portion of the PCR plate together with the first heating block, and the first heating block 310 corresponds to face the upper surface of the PCR plate. Thereafter, as illustrated in FIG. 7, when the second region is horizontally moved to the lower portion of the PCR plate together with the second heating block, the second heating block is horizontally moved and operated so as to face the upper surface of the PCR plate.

The horizontal movement operation of the constant temperature plate 350 may be performed in a sliding manner, and the constant temperature plate 350 may be implemented to move in contact with a sliding tape in contact with the side surface portion of the constant temperature plate 350.

Moreover, referring to FIGS. 6 and 7, FIGS. 6 and 7 are conceptual views illustrating the bottom of the temperature control module according to the present invention. As illustrated in FIGS. 6 and 7, the constant temperature plate 350 may include a plurality of through light-transmitting portions h which are disposed between the PCR plate 200 and the lower scanning module (not illustrated, reference numeral 500 in FIG. 1) and irradiated with excitation light emitted from the scanning module to transmit the light to the PCR plate 200 and guide the light of the scanning module 500 so that luminescence is detected.

Therefore, in the present invention, the nucleic acid extraction, PCR process, and detection process can be implemented by one system with the integrated system equipped with the above-described scanner, and a separate PCR plate structure can be implemented so that it can be applied to various diseases diagnosis.

FIG. 8 illustrates one embodiment of the PCR plate 200 applied to the present invention.

Referring to FIG. 8 and the conceptual views of FIGS. 2 and 3 described above, the PCR plate 200 according to the present invention includes a body portion 210 having at least one reaction well W1, . . . , Wn in which the primer dried product is accommodated on the plate-shaped surface, and a structure extending from one end of the body portion 210 and inserted into the nucleic acid extraction cartridge 100.

In particular, a structure may be implemented in which an insertion portion 220 having an injection hole h1 into which the PCR preliminary mixture is injected so as to be introduced from the nucleic acid extraction cartridge 100 is implemented. In addition, the PCR plate 200 may be implemented to have a connection portion which is connected to the injection hole h1 and may have a channel portion 231 provided on the body portion to be connected to the plurality of reaction wells.

Specifically, the PCR plate 200 includes the body portion 210 in which the plurality of reaction wells W1, . . . , Wn are implemented, as illustrated in FIG. 8. In this case, in the case of the reaction well, in the illustrated structure, the structure is implemented to have eight reaction wells, but the present invention is not limited thereto. That is, a structure having at least one reaction well may be implemented, and the structure of the reaction well can also be implemented as a concave pattern structure by processing the surface of the body portion 210.

In particular, in an exemplary embodiment of the present invention, as illustrated in FIG. 8, a partition pattern 215 that partitions the region of the reaction well is provided to protrude from the surface region of the body portion 210, and the primer prepared in a dried state in the reaction well and a PCR preliminary mixture injected from the nucleic acid extraction cartridge are dispersed and mixed in the reaction well.

In addition, the PCR plate 200 includes a cover member (not illustrated) that seals the upper portions of the plurality of reaction wells, and the cover member may be made of a transparent film material having light transmittance.

When the cover member is pressed against the surface of the reaction well to realize the inside of the reaction well as a cavity, the PCR preliminary mixture injected from the nucleic acid extraction cartridge later pushes an air layer present in the cavity and is injected to the inside of the reaction well.

In particular, in the present invention, as illustrated in the structure of FIG. 8, the channel portion 231 connected to the reaction well in the body portion 210 may be provided. The channel portion may be implemented to extend to the distal end 232 of the body portion via the body portion 210 from a start point of the channel portion 231 connected to the injection hole h1 and may be implemented to be connected to end portions of the plurality of reaction holes in a direction opposite to the insertion portion at the distal end 232.

That is, as in FIG. 2, when the nucleic acid extraction cartridge is injected through the injection hole h1 provided below the insertion portion, the channel is implemented in the direction x1 crossing the body portion from the start point of the channel portion 231, and the channel is branched off left and right at an end point of the body portion to be connected to the inlet to each reaction well. The reason for forming the channel in this way is that a small amount of air is present inside the reaction well region sealed by the cover member, the injected PCR preliminary mixture is filled up from a lower region Cb on the basis of a center line cx of the body portion as illustrated in the structure of FIG. 8, and the air layer is pushed up to an upper region Ca of the body portion.

Therefore, the mixture in which the PCR reaction to be performed is relatively disposed in the lower region Cb of the reaction well, and thus, the region where the heating block of the present invention performs pressurization and the region where the detection of the scanner module is performed are realized in the lower region Cb due to characteristics of the device, as illustrated in FIG. 8. Accordingly, it is possible to increase all of the precision of detection, efficiency of the PCR reaction, and efficiency of temperature control.

In addition, in the present invention, preferably, the PCR plate 200 is implemented with a synthetic resin material having high light transmittance. This is to increase the detection efficiency by configuring the scanner module with a material having high light transmittance according to the function of the above-described scanner module.

The materials may include various synthetic resin materials such as polypropylene (PP), polyethylene (PE), polyphthalamide (PPA), polymethyl methacrylate (PMMA), and polycarbonate (PC) but are not necessarily limited thereto, and any material may be used as long as the material can secure a certain light transmittance.

However, the PCR plate 200 can maintain a constant temperature due to the heat source applied from the constant temperature plate at the bottom portion, and in order to effectively maintain the temperature of the temperature control module directly applied to the PCR preliminary mixture, the nucleic acid solution, the dried primer/probe, or the PCR reactant including these which fill the inside of the reaction well, a thickness of the body portion 210 may be implemented in the range of 1.0 mm to 3.0 mm. When the thickness is less than 1.0 mm, high-temperature heat setting the first temperature is easily transferred to the lower portion of the body, which causes thermal interference with the constant temperature plate. Accordingly, temperature control is not easy. When the thickness exceeds 3.0 mm, a temperature of a material accommodated in the reaction well is easily controlled. However, it is not easy to control the temperature of the constant temperature plate at the bottom, and thus, it is difficult to maintain a constant temperature.

That is, in the present invention, as described above with reference to FIGS. 4 and 5, the first heating block 310 and the second heating block 320 are horizontally moved, the first pressing surface G1 or the second pressing surface G2 in contact with the surface of the reaction well come into contact with the upper surface of the partition pattern 215 and the cover member covering the partition pattern and perform the pressurization, and the set temperature becomes the first temperature or the second temperature to control the temperature of the reactant.

In addition, in the case of temperature circulation for the PCR plate 200, in the temperature control module according to the structure of FIGS. 2 and 3, in order to increase the temperature to the first temperature, the first heating block is horizontally moved to face the upper surface of the PCR plate, and after the first region of the constant temperature plate is horizontally moved together with the first heating block, the first heating block is moved below the PCR plate lower surface and comes into pressure-contact with the PCR plate lower surface. Moreover, in order to decrease the temperature to the second temperature, the upper surface of the PCR plate 200 is horizontally moved to face the second heating block, and after the second region of the constant temperature plate is horizontally moved together with the second heating block, the second heating block is moved below the lower surface of the PCR plate 200 and comes into pressure-contact with the lower surface. Accordingly, it is possible to simultaneously heat and cool the upper surface and the lower surface of the PCR plate 200. In the present invention, the constant temperature plate 350 and the first and second heating blocks 310 and 320 are implemented to be integrally moveable horizontally, and thus, the pressurization of the upper portion and the lower portion of the PCR plate 200 is performed at the same temperature at the same time.

Due to this operation, by simultaneously performing the contact pressurization on the upper and lower surfaces of the PCR plate, it is possible to realize double the efficiency compared to the constant temperature plate method maintained at a single temperature. Accordingly, the heating of the plate contained in the target is implemented simultaneously on the upper and lower surfaces, and thus, the inspection time can be reduced by half.

FIGS. 9 to 12 are diagrams for explaining, in detail, the structure and operation method of the constant temperature plate and the horizontal movement drive module.

FIG. 9 illustrates a structure in which the constant temperature plate 350 is seated in FIGS. 2 and 3, and FIG. 10 illustrates a structure in which only the constant temperature plate structure is separated.

Referring to FIGS. 9 and 10, the constant temperature plate 350 according to an embodiment of the present invention is disposed below the heating block structure constituting the temperature control module illustrated in FIGS. 2 and 3, and after the PCR plate 200 is disposed, when the first heating block 310 or the second heating block 320 of the temperature control module 300 pressurizes the PCR plate from the upper side by horizontal operation and vertical operation, the constant temperature plate 350 may have the same temperature as the first heating block 310 or the second heating block 320.

As illustrated in FIG. 9, the constant temperature plate 350 includes a separation portion SS which partitions the constant temperature plate 350 into the first region a1 maintaining the first temperature and the second region a2 maintaining the second temperature, and the first region a1 and the second region a2 are connected to each other on the basis of both ends a3 and a4 of the separation portion SS.

Connector structures Ca and Cb are mounted on one end of the constant temperature plate 350 to apply power or transmit a control signal.

In particular, the horizontal movement operation of the constant temperature plate 350 is implemented in a sliding manner and is implemented to be moved in contact with the sliding tape in contact with the side portion of the constant temperature plate 350. Accordingly, it is possible to implement the simplification of the structure as well as improve mobility.

In this case, a through hole H is provided in the second region a2 to allow the detected light of the scanning module 500 to scan the concentration of the amplified reactant to pass therethrough.

Temperature sensors Sa and Sb may be provided in the first region a1 and the second region a2 to measure and control the temperature of the corresponding region.

FIG. 11 is a view illustrating the lower surface of FIG. 10, in which connection connector portion Cc and Cd for applying a control signal and power are provided, the temperature sensors Sa and Sb are provided, and thus, it is possible to implement constant temperature maintenance of the first temperature and the second temperature.

To maintain the temperatures of the first region or the second region of the constant temperature plate, various heating units and a method of mounting various units such as a heating wire or a heating resistor inside the plate may be used. However, in an exemplary embodiment of the present invention, after implementing an electrode and a temperature sensor circuit on an epoxy printed circuit and applying the heating paint between the electrodes, the metal plates corresponding to the first and second regions are adhered to be pressed against each temperature sensor and the heating paint to achieve this effect.

FIG. 12 is an upper plan conceptual view for describing the operation method described above in more detail with reference to FIGS. 6 and 7.

In the present invention, the horizontal movement drive module 400 may be further provided, which horizontally moves the constant temperature plate 350 to the lower portion of the PCR plate 200.

As illustrated in FIGS. 2 and 3, as described above, the horizontal movement drive module 400 may include the moving bar 420 and the driving motor unit 410 which are coupled to one end of the constant temperature plate 350, and the conversion plate 430 which converts the rotational force of the driving motor unit 410 into the horizontal movement force of the moving bar 420.

As illustrated in FIG. 12, the PCR plate 200 is inserted into the nucleic acid extraction cartridge and has the channel coupled thereto, the nucleic acid solution extracted from the nucleic acid extraction cartridge 100 is injected into the injection hole h1, and the extracted nucleic acid solution is moved to the PCR plate 200 in which the extracted nucleic acid solution is accommodated to be injected in at least one reaction well accommodating the PCR dried mixture containing the primer, the primer/probe, or the primer probe.

Thereafter, the first heating block 310 or the second heating block 320 of the temperature control module 300 of the present invention for forming the first temperature or the second temperature is lowered to the reaction well portion of the PCR plate 200.

In this case, the horizontal movement drive module 400 horizontally moves the constant temperature plate 350 and the temperature control module 300 together, and the PCR plate is disposed to be inserted between the constant temperature plate 350 and the temperature control module 300.

When the heating block horizontally moved through the horizontal movement drive module 400 pressurizes the PCR plate, the first region or the second region of the constant temperature plate having the set temperature (first temperature or second temperature) corresponding to the temperature of the heating block is disposed to correspond naturally.

That is, when the first region a1 of the constant temperature plate 350 is horizontally moved to the lower portion of the PCR plate 200, the first heating block (310 in FIG. 2) is moved horizontally at the same time and corresponds to face the upper surface of the PCR plate, and then the heating block is lowered to come into contact with the upper surface of the PCR plate.

In addition, when the second region a2 is horizontally moved to the lower portion of the PCR plate and disposed, the second heating blocks (320 in FIG. 2) move horizontally at the same time and operate so as to face the upper surface of the PCR plate, and thereafter, the heating block is lowered to come into contact with the upper surface of the PCR plate.

In other words, in the case of temperature circulation for the PCR plate 200, in order to increase the temperature to the first temperature, the first heating block is horizontally moved to face the upper surface of the PCR plate, and after the first region of the constant temperature plate is horizontally moved, the first heating block is moved below the PCR plate lower surface and is driven to come into pressure-contact with the PCR plate lower surface.

In addition, in order to decrease the temperature to the second temperature again, the upper surface of the PCR plate 200 is horizontally moved to face the second heating block, and after the second region of the constant temperature plate is horizontally moved, the second heating block is moved below the lower surface of the PCR plate 200 and comes into pressure-contact with the lower surface. Accordingly, it is possible to simultaneously heat and cool the upper surface and the lower surface of the PCR plate 200.

In this way, by performing the contact pressurization on the upper and lower surfaces of the PCR plate at the same time, it is possible to realize double the efficiency compared to the constant temperature plate method maintained at a single temperature.

Hereinafter, the nucleic acid extraction cartridge 100 implementing the PCR preliminary mixture containing the nucleic acid extract on the PCR plate in the present invention will be described with reference to FIGS. 13 to 19.

FIG. 13 is a perspective view of the nucleic acid extraction cartridge of the present invention and illustrates a structure in which the PCR plate described above is inserted. FIG. 10 is an exploded perspective view of FIG. 9, and FIG. 11 illustrates an internal structure of a cartridge cover portion R1 in the structure of FIG. 10 (in the present embodiment, a structure in which a gene amplification plate has two reaction wells will be described).

Referring to FIGS. 13 to 15, the nucleic acid extraction cartridge 100 according to the present invention may include the cartridge cover portion R1 having a plurality of accommodating portions 22, 23, 24, 25, and 26 which are portioned to store solutions required for DNA extraction and a cartridge body portion R2 which is coupled to the cartridge cover portion R1 in an insertion manner and includes a reaction accommodating portion 11 for reacting the solution introduced from the accommodating portions with the sample or cleaning the solution.

In this case, a piston 18 may be provided which injects the PCR preliminary mixture purified in the reaction accommodating portion 11 into the injection hole h1 of the PCR plate 200 which is coupled to be inserted into the cartridge body portion R2.

The operation of the nucleic acid extraction cartridge of the present invention will be described with reference to FIGS. 14, 15, and 17. FIG. 16 is a perspective view of FIG. 13 illustrating the internal structure after coupling.

In the nucleic acid extraction cartridge of the present invention, a rotary valve 19 having a channel 19-1 formed therein is mounted on a bottom surface of the cartridge body portion R2, and when the rotary valve is rotated, the accommodating portions 11, 12, 13, 14, 15, 16, and 17 of the cartridge body portion R2 may be connected to the channel of the rotary valve 19. After the channel is connected to a specific accommodating portion, the piston 18 is operated to take the solution contained in the accommodating portion, and thus, the solution is transferred to another accommodating portion or PCR plate 200.

Referring to FIGS. 14 and 15, the accommodating portions 22, 23, 24, 25, and 26 containing each solution required for DNA extraction are formed inside the cartridge cover portion R1, and a bottom surface of each of the accommodating portions is sealed with a film or the like, and is designed to be easily penetrated by a penetrating needle (10-1 in FIG. 12) of a main body accommodating portion. In addition, five holes 21-1, 21-2, 27, 28, and 29 are formed.

A binding buffer is accommodated in a first accommodating portion 22 of the cartridge cover portion R1, a first cleaning buffer is accommodated in a second accommodating portion 23, a second cleaning buffer is accommodated in a third accommodating portion 24, a third cleaning buffer is accommodated in a fourth accommodating portion 25, and an elution buffer is accommodated in a fifth accommodating portion 26.

The PCR plate 200 is covered with a film formed of a transparent plastic material (polyethylene, polypropylene, PET, or the like), and the dried PCR primer/probe or the PCR mixture including these is contained inside the reaction well, which is the same as the structure of FIG. 8 described above.

The operation of the nucleic acid extraction cartridge of the present invention may proceed in the following order.
1. Input of Biological Sample
The cartridge body portion R2, the cartridge cover portion R1, and the PCR plate 200 are mounted in automated equipment to be described later in a combined state, and a biological sample (blood) is input into a first hole 21-1 illustrated in FIG. 14.
2. Emission of Nucleic Acid from Cell and Binding to Bead As illustrated in FIG. 17, the binding buffer of the first accommodating portion 22 is input to the reaction accommodating portion 11 through the rotation of the rotary valve 19 and the operation of the piston 18 disposed at the lower portion of the cartridge body portion R2 and mixed with the biological sample and a bead (magnetic bead coated with silica) of the magnetic tablet (MT).

The MT used in the present invention is mounted on the distal end of a through pipe extending into the inside of the reaction accommodating portion 11 of the cartridge body portion R2, and the nucleic acid extracted from the cells contained in the biological sample functions to bind the nucleic acid with the surface of the magnetic bead dispersed by dissolving the magnetic tablet.

In this case, instead of the magnetic tablet, the magnetic beads may be suspended in a binding buffer and used.

After that, when a sonication tip is put into the sealed second hole 21-2 of the cartridge body portion R2 and ultrasonic waves are applied, the ultrasonic waves are transmitted through the plastic, the biological sample, tablet, and binding buffer are mixed to homogenize the reaction solution, and at this time, the biological tissues contained in the biological sample are also crushed to release the nucleic acid and the released nucleic acid is bound to the surface of the bead.

When a magnetic bar is inserted into the third hole 27 of the cartridge body portion R2, the beads are fixed to the wall of the reaction accommodating portion, and the remaining reaction solution is transferred to the first accommodating portion through the rotation of the rotary valve and the operation of the piston.
3. First Cleaning The first cleaning buffer of the second accommodating portion 23 is put into the reaction accommodating portion 11 through the rotation of the rotary valve of the cartridge body portion R2 and the operation of the piston illustrated in FIG. 16 and mixed with the nucleic acid-bound beads.

Thereafter, when the magnetic bar is removed from the third hole 27 of FIG. 14 and ultrasonic waves are applied to the sonication tip in the second hole 21-2, the first cleaning is performed. Due to this first cleaning, substances non-specifically bound to the beads other than nucleic acids are cleaned away.

The magnetic bar is inserted into the third hole 27 so that the beads are fixed to the wall surface of the reaction accommodating portion, and a primary cleaning liquid is transferred to the second accommodating portion 23 through the rotation of the rotary valve and the operation of the piston.
4. Second Cleaning The second cleaning buffer of the third accommodating portion 24 is input into the reaction accommodating portion 11 through the rotation of the rotary valve of the cartridge body portion R2 illustrated in FIG. 16 and the operation of the piston, and mixed with the nucleic acid-bound beads.

Thereafter, when the magnetic bar is removed from the third hole 27 of FIG. 14 and ultrasonic waves are applied to the sonication tip of the second hole 21-2, secondary cleaning is performed. Due to this second cleaning, substances non-specifically bound to the beads other than nucleic acids are cleaned away.

A magnetic bar is input to the third hole 27 so that the beads are fixed to the wall of the reaction accommodating portion, and a secondary cleaning liquid is transferred to the third accommodating portion 24 through the rotation of the rotary valve and the operation of the piston.

5. Third Cleaning

The third cleaning buffer of the fourth accommodating portion 25 is input to the reaction accommodating portion 11 through the rotation of the rotary valve of the cartridge body portion R2 illustrated in FIG. 16 and the operation of the piston, and is mixed with the nucleic acid-bound beads.

Thereafter, when the magnetic bar is removed from the third hole 27 of FIG. 14 and ultrasonic waves are applied to the sonication tip in the second hole 21-2, third cleaning is performed. Due to this third cleaning, substances non-specifically bound to the beads other than nucleic acids are cleaned away.

A magnetic bar is input to the third hole 27 so that the beads are fixed to the wall of the reaction accommodating portion, and a tertiary cleaning liquid is transferred to the fourth accommodating portion 25 through the rotation of the rotary valve and the operation of the piston.

6. Nucleic Acid Elution

The elution buffer of the fifth accommodating portion 26 is input to the reaction accommodating portion 11 through the rotation of the rotary valve of the cartridge body portion R2 illustrated in FIG. 16 and the operation of the piston, and is mixed with the nucleic acid-coupled beads.

Then, when the magnetic bar is removed from the third hole 27 of FIG. 14, the sonication tip is inserted into the second hole 21-2, and ultrasonic waves are applied, the nucleic acid bound to the bead surface is dissolved in the elution buffer.

7. Generation of PCR Preliminary Mixture

The magnetic bar is inserted into the third hole 27 so that the beads are fixed to the wall of the reaction accommodating portion, the rotation of the rotary valve and the small piston are selected, the nucleic acid-dissolved elution buffer is put into the sixth accommodating portion 17 using the small piston and mixed with the PCR material (a mixture of polymerase, d nucleoside triphosphate (dNTP), or the like) accommodated in the sixth accommodating portion, and thus, the PCR preliminary mixture is generated. The "PCR preliminary mixture" used in the present invention is defined and used as embodied by the above materials. The above process is omitted when the PCR reaction including the primer/probe is dried in each well of the PCR plate, and the nucleic acid eluate is directly injected into the PCR plate as illustrated below.

8. Transfer to PCR Plate

The PCR preliminary mixture generated in the sixth accommodating portion is input to the PCR plate 200 through the rotation of the rotary valve of the cartridge body portion R2 and the operation of the piston illustrated in FIG. 16 and is mixed with the primer/probe contained in the PCR plate 200. In this input process, as illustrated in FIG. 19, the PCR preliminary mixture moves along the channel Y of the rotary valve by the pressure of the piston 18 and is injected into the injection hole h1.

Thereafter, a heating rod is inserted into the fourth hole 29 to heat the cover film of an inlet portion of the PCR reaction plate under pressure, and thus, the PCR reaction plate is sealed.

9. PCR Reaction

Finally, the PCR plate 200 contains the extracted nucleic acid, polymerase, dNTP, primer/probe, and other buffers from the biological sample.

Therefore, the PCR reaction is performed by applying the pressure and heat to the PCR plate 200 through the temperature control module of the present invention described above.

FIGS. 20 to 23 illustrate the overall structure and layout of the device constituting the PCR system of the present invention described above.

As illustrated in FIG. 20, when the nucleic acid extraction cartridge 100 is mounted inside the PCR system according to the present invention, the PCR plate 200 described above is seated on a side surface. The portion in which the reaction well corresponding to the body portion of the PCR plate 200 exists is exposed to the outside, and the above-described temperature control module 300 is disposed thereon.

FIG. 21 is an enlarged view of the coupling arrangement of the main portion of the present invention in FIG. 20, and FIG. 22 is a conceptual view of a vertical section of the portion of FIG. 21 for describing the arrangement of the main components. FIG. 23 is a lateral perspective cross-sectional conceptual view of FIG. 22.

As illustrated in FIGS. 21 to 23, the PCR preliminary mixture containing the nucleic acid extracted from the inside of the nucleic acid extraction cartridge 100 according to the present invention is injected into the PCR plate 200 in which the reaction well is implemented. The first pressing surface G1 corresponding to the reaction well surface is implemented on the upper portion of the PCR plate 200, the first heating block 310 maintained at a temperature required for denaturation by the heating unit is disposed, and the second heating block 320 in which the region horizontally moved and pressured is implemented to be changed is disposed adjacently. Accordingly, the PCR preliminary mixture injected into the reaction well is directly heated by a heating block to meet the first temperature of 95° C. required for the denaturation or the second temperature of 55° C. required for annealing.

In addition, as illustrated in FIGS. 22 and 23, the constant temperature plate 350 is disposed below the PCR plate 200 to maintain the temperature of the PCR plate 200 at a constant temperature level.

The scanning module 500 is disposed below the constant temperature plate 350 so that light L irradiated by a light irradiation unit E1 reaches the PCR plate 200 via the light transmission unit H of the constant temperature plate 350, and thus, fluorescence detection is performed.

In the embodiment of the present invention, as described above, in the case of increasing the temperature by pressing against the first heating block of the first temperature (for example, 95° C.) by the temperature control module, or in the case of pressing against the second heating block of the second temperature (for example, 55° C.), it becomes much easier to control the temperature of the internal amplification reaction when the PCR plate 200 is maintained in a constant temperature range. Accordingly, constantly maintaining the temperature of the above-described constant temperature plate at the second temperature is a very important factor for increasing the reliability of the reaction. When the temperature of the PCR plate is raised to 95° C., the temperature of the PCR plate can quickly reach 95° C. within 2 to 3 seconds by increasing the heat transfer rate by pressing the first temperature block and the first constant temperature zone against each other.

When performing RT/PCR to detect RNA targets, the PCR preliminary mixture or PCR plate containing the RT-PCR reaction dry matter is used. After a low temperature block is adjusted to the RT reaction temperature to be pressed against the PCR reaction plate and maintain pressing for as long as the RT reaction time, the PCR reaction may be performed after performing the reverse transfer reaction.

The presence or absence of the amplified nucleic acid or the concentration of the amplified nucleic acid is determined through the PCR reaction, this information may be used for diagnosis, and in this case, the presence or absence, or concentration of the amplified nucleic acid can be achieved using a conventional nucleic acid detection method.

For example, a method of using a DNA minor groove which is a DNA intercalation dye and a SYBR green which is an insertion fluorescent dye, a method of scanning pieces of excitation light in various wavelength bands and fluorescence corresponding to the excitation light using probes with various fluorescence and quenchers attached, or the like may be used, but the present invention is not limited thereto.

In the above, the present invention is described on the basis of an exemplary embodiment, but a technical spirit of the present invention is not limited thereto. That is, it is clear to those of ordinary skill in the art to which the present invention pertains that modifications or changes can be made within the scope described in claims, and the modifications and variations are intended to fall within the scope of the appended claims.

REFERENCE SINGS LIST

100: nucleic acid extraction cartridge
200: PCR plate
210: body portion
220: insertion portion
300: temperature control module
310: first heating block
320: second heating block
330: drive module
340: cooling fan unit
350: constant temperature plate
400: horizontal movement drive module
500: scanning module
W: reaction well

The invention claimed is:

1. A polymerase chain reaction (PCR) system comprising:
a nucleic acid extraction cartridge (100) configured to extract a nucleic acid of a biological sample via a nucleic acid extraction reagent stored therein;
a PCR plate (200) having a channel coupled to the nucleic acid extraction cartridge and at least one reaction well (W) which accommodates a PCR dried mixture containing a primer, a primer/probe, or a primer probe and receives a nucleic acid solution extracted from the nucleic acid extraction cartridge (100); and
a temperature control module (300) disposed above the PCR plate (200), adjacent to the reaction well (W) to apply different temperatures, and having a pair of heating blocks (310, 320) that are movable horizontally and vertically,
wherein the temperature control module (300) includes:
a first heat block including a first pressing surface (G1) corresponding to a surface of the reaction well and maintained at a temperature (hereinafter, referred to as a "first temperature") required for denaturation;
a second heating block (320) disposed at a position corresponding to the first heating block (310) and spaced apart from the first heating block (310), including a second pressing surface (G2) corresponding to the surface of the reaction well, and maintained at a temperature (hereinafter, referred to as a "second temperature") required for annealing; and
a drive module (330) configured to perform horizontal movements and vertical movements of the first heating block (310) and the second heating block (320).

2. The PCR system of claim 1, further comprising a cooling fan unit (340) configured to control thermal radiation conduction between the first heating block (310) and the second heating block (320).

3. The PCR system of claim 2, wherein the first heating block (310) and the second heating block (320) are disposed to be spaced apart from each other and cross each other according to an operation of the drive module (330) to perform the vertical movement.

4. The PCR system of claim 2, wherein the first heating block (310) or the second heating block (320) further includes a cooling pattern portion (311, 321) formed on one side surface thereof.

5. The PCR system of claim 2, wherein the first heating block (310) and the second heating block (320) maintain a set temperature at the first temperature or the second temperature through a temperature sensor and a heating unit.

6. The PCR system of claim 2, wherein the drive module (330) includes a guide member (331, 332) passing through the first heating block (310) and the second heating block (320), and the first heating block (310) and the second heating block (320) perform the vertical movement along the guide member (331, 332).

7. The PCR system of claim 5, further comprising an elastic member (S1, S2) disposed below the guide member (331, 332).

8. A polymerase chain reaction (PCR) system comprising:
a temperature control module (300) including a pair of heating blocks (310, 320) horizontally and vertically movable to apply a first temperature and a second temperature, which are different from each other, to an upper portion of a PCR plate (200) which receives a nucleic acid solution and accommodates a PCR dried mixture containing a primer, a primer/probe, or a primer probe; and
a constant temperature plate (350) disposed below the PCR plate (200) to maintain a temperature of the PCR plate (200) at the first temperature or the second temperature,
wherein the constant temperature plate (350) includes a first region heated to a first temperature and a second region spaced apart from the first region and heated to a second temperature,
a first pressing surface (G1) of the first heating block 310 is disposed to correspond to an upper portion of the first region, and
a second pressing surface (G2) of the second heating block 320 is disposed to correspond to an upper portion of the second region.

9. The PCR system of claim 8, wherein the temperature control module (300) and the constant temperature plate 350 are integrated with each other via the guide member (331, 332).

10. The PCR system of claim 9, further comprising a horizontal movement drive module (400) which horizontally moves the constant temperature plate (350) and the temperature control module (300) to a lower portion of the PCR plate (200).

11. The PCR system of claim 8, wherein the constant temperature plate (350) includes a separation portion (SS) partitioning the constant temperature plate (350) into the first region and the second region, and
the first region and the second region are connected on the basis of both ends of the separation portion (SS).

12. The PCR system of claim 8, wherein, in the constant temperature plate (350), a temperature sensor and a heating element circuit are formed on a printed circuit board (PCB), and metal plates each corresponding to one of the first region and the second region are bonded so that the heating element and the temperature sensor are pressed against each other.

13. The PCR system of claim 8, wherein a horizontal movement of the constant temperature plate (350) is performed in a sliding manner, and the constant temperature plate (350) is moved to come into contact with a sliding tape in contact with a side surface portion of the constant temperature plate (350).

14. The PCR system of claim 8, wherein, when the first region is moved horizontally to a lower portion of the PCR plate and disposed, the first heating block is moved from an upper side to a lower side, faces an upper surface of the PCR plate, and is pressurized, and when the second region is moved horizontally to the lower portion of the PCR plate and disposed, the second heating block is moved from the upper side to the lower side, faces the upper surface of the PCR plate, and is pressurized.

15. The PCR system of claim 12, wherein, when temperature circulation is performed on the PCR plate (200), the first heating block is horizontally moved to face an upper surface of the PCR plate, and a lower surface of the PCR plate is moved below the first heating block after the first region of the constant temperature plate is horizontally moved and pressurized to come into contact with the first heating block in order to increase the first temperature, the upper surface of the PCR plate (200) is horizontally moved to face the second heating block, and the lower surface of the PCR plate is moved below the second heating block after the second region of the constant temperature plate is horizontally moved and pressurized to come into contact with the second heating block in order to decrease the second temperature, and an upper surface and a lower surface of the PCR plate (200) are heated and cooled at the same time.

16. The PCR system of claim 8, wherein the constant temperature plate (350) further includes a temperature sensor (T1, T2) for sensing a temperature of the constant temperature plate at at least one location and a temperature sensor portion (351) including a control module (Cp) for controlling a change in set temperature.

17. The PCR system of claim 8, comprising a scanning module (500) which is disposed below the PCR plate (200) and scans a concentration of a reactant amplified in the reaction well (W) with pieces of excitation light in various wavelength bands and fluorescence corresponding to the excitation light.

18. The PCR system of claim 17, wherein the constant temperature plate (350) includes a plurality of through structures having light-transmitting portions (H) along which detected light of the scanning module (500) is guided.

* * * * *